(12) United States Patent
Zalipsky et al.

(10) Patent No.: US 7,150,882 B2
(45) Date of Patent: *Dec. 19, 2006

(54) ENHANCED CIRCULATION EFFECTOR COMPOSITION AND METHOD

(75) Inventors: Samuel Zalipsky, Redwood City, CA (US); Martin C. Woodle, Menlo Park, CA (US); Francis J. Martin, San Francisco, CA (US); Yechezkel Barenholz, Jerusalem (IL); Herve Bercovier, Jerusalem (IL)

(73) Assignee: Alza Corporation, Mountain View, CA (US)

( * ) Notice: Subject to any disclaimer, the term of this patent is extended or adjusted under 35 U.S.C. 154(b) by 142 days.

This patent is subject to a terminal disclaimer.

(21) Appl. No.: 10/832,636

(22) Filed: Apr. 26, 2004

(65) Prior Publication Data

US 2004/0247663 A1 Dec. 9, 2004

Related U.S. Application Data

(63) Continuation of application No. 10/438,502, filed on May 14, 2003, which is a continuation of application No. 09/877,978, filed on Jun. 8, 2001, now Pat. No. 6,586,002, which is a continuation of application No. 08/480,332, filed on Jun. 7, 1995, now Pat. No. 6,180,134, which is a continuation-in-part of application No. 08/316,436, filed on Sep. 29, 1994, now abandoned, which is a continuation-in-part of application No. 08/035,443, filed on Mar. 23, 1993, now Pat. No. 6,326,353.

(51) Int. Cl.
*A61K 9/127* (2006.01)

(52) U.S. Cl. ............ 424/450; 424/85.8; 424/85.2; 424/85.4; 424/812; 530/391.1; 530/350

(58) Field of Classification Search ............ 424/450, 424/85.8, 85.2, 85.4, 812; 530/391, 391.1, 530/350, 331–324
See application file for complete search history.

(56) References Cited

U.S. PATENT DOCUMENTS

| | | | |
|---|---|---|---|
| 4,179,337 A | 12/1979 | Davis et al. | |
| 4,429,008 A | 1/1984 | Martin et al. | |
| 4,948,590 A | 8/1990 | Hawrot et al. | |
| 5,013,556 A | 5/1991 | Woodle et al. | |
| 5,092,885 A | 3/1992 | Yamada et al. | |
| 5,122,614 A | 6/1992 | Zalipsky | |
| 5,140,013 A | 8/1992 | Gaudreault et al. | |
| 5,149,794 A | 9/1992 | Yatvin et al. | |
| 5,527,528 A | 6/1996 | Allen et al. | |
| 6,180,134 B1 * | 1/2001 | Zalipsky et al. | 424/450 |
| 6,326,353 B1 * | 12/2001 | Zalipsky et al. | 514/11 |
| 6,586,002 B1 * | 7/2003 | Zalipsky et al. | 424/450 |

FOREIGN PATENT DOCUMENTS

| | | |
|---|---|---|
| EP | 0 339 504 | 11/1989 |
| EP | 0 428 486 | 5/1991 |
| WO | WO 90/14103 | 11/1990 |

OTHER PUBLICATIONS

Maruyama, Journal of Liposome Research 7(4) 363 (1997).*
Blume, G., et al., *Biochimica et Biophysica Acta* 1149:180-184 (1993).
Cross, et al., *Infect Immun* 61(7):2741-2747, (1993).
deAzavedo, J.C.S., et al., pp. 419-430 (1985).
Endo, S., et al., *Clinical Therapeutics* 14(1):64-67 (1992).
Feist, W., et al., *FEMS Microbiology Immunology* 89:73-90 (1992).
Fitzer-SchillerReuter, G., "Centocor Stops Trials of Flagship Drug", Washington Post Financial section, pp. D3 Jan. 19, 1993.
Harris, et al., *Trends Biotechnol* 11(2):42-44 (1993).
Hayashi, T., and Y. Ikada, *Biotechnology and Polymers* (C.G. Gebelein, Ed., Plenum Press, New York), pp. 321-332 (1991).
Hershfield, M.S., et al., *New England J. Med.* 316(10):589-595 (1987).
Hird, *Genes & Cancer* pp. 183-189 (1990).
Hunefield, G., *Anaesthesiol Reanimat* 14(3):131-153 (1989).
Iwamoto, Y., et al., *Science 238*: 1132-1134 (1987).
Katre, N.V., et al., *Proc. Natl. Acad. Sci. USA* 84:1487-1491 (1987).
Kawasaki, K., et al., *Biochemical and Biophysical Research Communications* 174(3):1159-1162 (1991).
Klibanov, A.L., et al., *Am. J. Physiol. Suppl.* 261:60-65 (1991).
Klibanov, A.L. and Huang, L., *Journal of Liposome Research* 2(3):321-334 (1992).
Manson, W.L., et al., Burns 18(2):98-102 (1992).
Maruyama, K., et al., *Proc. Natl. Acad. Sci. USA* 87:5744-5748 (1990).
Munster, A., et al., *J Burn Care Rehabil* 10(4);327-330 (1989).
Murata, J., et al., *Int. J. Biol. Macromol.* 11:97-99 (1989).
Nitecki, D.E., and L. Aldwin, *Biotechnology and Polymers* C.G. Gebelein, Ed., Plenum Press, New York) pp. 295-299 (1991).
Osband, et al., *Imm Today* 11(6):193-195, (1990).
Saiki, I., et al., *Br. J. Cancer* 60:722-728 (1989).
Sastry, P.A., et al., *Journal of Bacteriology* 164(2):571-577 (1985).
Tam, J.P., *Proc. Natl. Acad. Sci. USA* 85:5409-5413 (1988).
Veronese, F.M., et al., *Applied Biochem. and Biotech.* 11:141-149 (1985).
Zalipsky, S., et al., *Eur. Polym. J.* 19(12):1177-1183 (1983).

* cited by examiner

*Primary Examiner*—Sheela J. Huff
(74) *Attorney, Agent, or Firm*—Perkins Coie LLP

(57) ABSTRACT

A liposome composition comprising small, surface-bound effector molecules is disclosed. The liposomes have a surface layer of hydrophilic polymer chains, for enhanced circulation time in the bloodstream. The effector molecules are attached to the distal ends of the polymer chains. In one embodiment, the effector is polymyxin B, for treatment of septic shock.

48 Claims, 13 Drawing Sheets

I

II

III

| SEQ ID NO:1 | RIQRGPGRAFVTIGK |
| SEQ ID NO:2 | NNTRKSIRIQRGPGRAFVTIGKIG |
| SEQ ID NO:3 | RAFVTIGK |
| SEQ ID NO:4 | TKGPGRVIYATGQ |
| SEQ ID NO:5 | HIGPGRAFYTTKN |
| SEQ ID NO:6 | YIGSR |
| SEQ ID NO:7 | CDPGYIGSR |
| SEQ ID NO:8 | GRGDS |
| SEQ ID NO:9 | RGDSGYIGSR |
| SEQ ID NO:10 | YCGSR |

SEQUENCE LISTING

```
<160> NUMBER OF SEQ ID NOS: 10

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Arg Ile Gln Arg Gly Pro Gly Arg Ala Phe Val Thr Ile Gly Lys
1               5                   10                  15

<210> SEQ ID NO 2
<211> LENGTH: 24
<212> TYPE: PRT
<213> ORGANISM: Artificial Sequence
<220> FEATURE:
<223> OTHER INFORMATION: synthetic peptide

<400> SEQUENCE: 2

Asn Asn Thr Arg Lys Ser Ile Arg Ile Gln Arg Gly Pro Gly Arg Ala
1               5                   10                  15

Phe Val Thr Ile Gly Lys Ile Gly
            20

<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3

Arg Ala Phe Val Thr Ile Gly Lys
1               5

<210> SEQ ID NO 4
<211> LENGTH: 13
<212> TYPE: PRT
<213> ORGANISM: Artificial Sequence
<220> FEATURE:
<223> OTHER INFORMATION: synthetic peptide

<400> SEQUENCE: 4

Thr Lys Gly Pro Gly Arg Val Ile Tyr Ala Thr Gly Gln
1               5                   10

<210> SEQ ID NO 5
<211> LENGTH: 13
<212> TYPE: PRT
<213> ORGANISM: Artificial Sequence
<220> FEATURE:
<223> OTHER INFORMATION: synthetic peptide

<400> SEQUENCE: 5

His Ile Gly Pro Gly Arg Ala Phe Tyr Thr Thr Lys Asn
1               5                   10

<210> SEQ ID NO 6
<211> LENGTH: 5
```

```
<212> TYPE: PRT
<213> ORGANISM: Artificial Sequence
<220> FEATURE:
<223> OTHER INFORMATION: synthetic peptide

<400> SEQUENCE: 6

Tyr Ile Gly Ser Arg
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic peptide

<400> SEQUENCE: 7

Cys Asp Pro Gly Tyr Ile Gly Ser Arg
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic peptide

<400> SEQUENCE: 8

Gly Arg Gly Asp Ser
1               5

<210> SEQ ID NO 9
<211> LENGTH: 10
<212> TYPE: PRT
<213> ORGANISM: Artificial Sequence
<220> FEATURE:
<223> OTHER INFORMATION: synthetic peptide

<400> SEQUENCE: 9

Arg Gly Asp Ser Gly Tyr Ile Gly Ser Arg
1               5                   10

<210> SEQ ID NO 10
<211> LENGTH: 5
<212> TYPE: PRT
<213> ORGANISM: Artificial Sequence
<220> FEATURE:
<223> OTHER INFORMATION: synthetic peptide

<400> SEQUENCE: 10

Tyr Cys Gly Ser Arg
1               5
```

ENHANCED CIRCULATION EFFECTOR COMPOSITION AND METHOD

This application is a continuation of U.S. application Ser. No. 10/438,502 filed May 14, 2003, now pending; which is a continuation of U.S. application Ser. No. 09/877,978 filed Jun. 8, 2001, now U.S. Pat. No. 6,586,002; which is a continuation of U.S. application Ser. No. 08/480,332 filed Jun. 7, 1995, now U.S. Pat. No. 6,180,134; which is a continuation-in-part of U.S. application Ser. No. 08/316,436 filed Sep. 29, 1994, now abandoned; which is a continuation-in-part of U.S. application Ser. No. 08/035,443 filed Mar. 23, 1993, now U.S. Pat. No. 6,326,353; all of which are incorporated herein in its entirety by reference.

FIELD OF THE INVENTION

The present invention relates to an enhanced-circulation effector composition and method for treating a subject with small effector molecules which are normally subject to rapid renal clearance from the bloodstream.

BACKGROUND OF THE INVENTION

A number of emerging or current therapies involve intravenous injection of small (less than 50 Kdaltons) protein, polypeptide or polysaccharide effectors. Such effectors can include $F_{ab}$ antibody fragments for use in active immunity, cytokines and cellular growth factors for stimulating immunological inflammatory responses, hormones, and polysaccharides, which are capable of interacting with endothelial cell receptors to competitively block neutrophil binding to activated endothelial cells lining the blood vessel (Katre, N. V., et al., *Proc. Natl. Acad. Sci. USA* 84:1487–1491 (1987); Philips, M. L., et al., *Science* 250:1130–1132 (1990); Waldmann, T. A., *Annu. Rev. Immunol.* 10:675–704 (1992)).

Other small polypeptide effectors have been proposed for use in blocking viral infection of target cells in the blood, such as a CD4+ glycopeptide which is effective to inhibit binding of human immunodeficiency virus (HIV) to $CD4^+$ cells (Capon, D. J. and Ward, R. H. R., Ann. Rev. Immunol. 9:649–678 (1991); Janeway, C. A., Ann. Rev. Immunol. 10:645–674 (1992)).

Polymyxin B, a small basic peptide which is rapidly excreted by the kidneys, is known to react with and neutralize gram-negative bacterial endotoxins, specifically *E. coli* 0111:B4 liposaccharide (LPS) (Baldwin, G., et al., *J. Infect. Diseas.* 164:542–549 (1991)). It is not often administered parenterally as a treatment for septic shock syndrome, because high doses of polymyxin B are required for effective treatment. High doses can be fatal, due to renal toxicity, making advanced stages of septic shock difficult to treat.

The problem of rapid renal clearance observed with polymyxin B is also applicable to other small peptides, such as those discussed above, which have been used for parenteral treatment of disease. In general, circulating proteins which are smaller than about 50–60 Kdaltons will be cleared by the kidneys with a lifetime of less than 1–2 hours.

In some cases, peptide molecular weight can be increased above the threshold 50–60 Kdalton size by derivatizing the peptide with biologically compatible polymers, such as polyethyleneglycol (PEG) (e.g., U.S. Pat. No. 4,179,337). However, this strategy may not always be effective for small effectors, e.g., those with molecular weights less than about 5–10 Kdalton. Moreover, derivatizing a polypeptide with a plurality of PEG chains may destroy or reduce the polypeptide activity, and/or mask key activity sites of the polypeptide.

SUMMARY OF THE INVENTION

The invention includes, in one aspect, a liposome composition for use in treating a subject with a polypeptide or polysaccharide effector which is effective as a pharmacological agent when circulating in free form in the bloodstream, but which is rapidly removed from the bloodstream by renal clearance in free form. The composition includes liposomes having an outer surface layer of polyethylene glycol chains and the effector covalently attached to the distal ends of the chains. A preferred polymer is polyethylene glycol having a molecular weight between about 1,000 and 10,000 daltons.

Preferred effectors include:

(a) an antibody $F_{ab}$ fragment having neutralizing activity against a given pathogen present in the bloodstream, for use in treating the subject for infection by the pathogen;

(b) a CD4 glycoprotein, for use in treating the subject for infection by human immunodeficiency virus (HIV);

(c) a cytokine or a cellular growth factor, for use in stimulating an immune response in the subject;

(d) a polysaccharide which binds to endothelial leukocyte adhesion molecule (ELAM), for use in treating inflammation related to neutrophil recruitment and tissue infiltration;

(e) IL-1 inhibitor or IL-1RA, for treating a subject to achieve immune-response suppression;

(f) polymyxin B or polymyxin B decapeptide, for treating the subject for septic shock;

(g) a peptide hormone, for treating a subject to regulate cellular growth; and (h) a peptide, for inhibiting a ligand-receptor cell-binding event.

In one specific embodiment, the invention includes a method of preventing progression of gram-negative bacteremia to septic shock and a method of treating acute septic shock by administering to a subject, a liposome composition containing liposomes having an outer layer of polyethylene glycol (PEG) chains and polymyxin B attached to the distal ends of the polymer chains.

In another aspect, the invention includes a liposome composition for use in preventing rapid removal from the bloodstream of a polypeptide or polysaccharide effector by renal clearance. The composition includes liposomes having an outer layer of polyethylene glycol chains, and attached to the distal ends of the chains, is one of the above effectors (a)–(h).

These and other objects and features of the invention will become more fully apparent when the following detailed description of the invention is read in conjunction with the accompanying drawings.

DETAILED DESCRIPTION OF THE INVENTION

I. Definitions

Figure 1A:
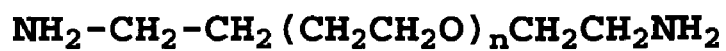
FIGS. 1A–1B show steps for the synthesis of a maleimide of a DSPE carbamide of polyethylene glycol (PEG) bis (amine)
Figure 1A:
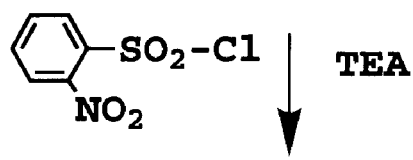
Figure 1A:
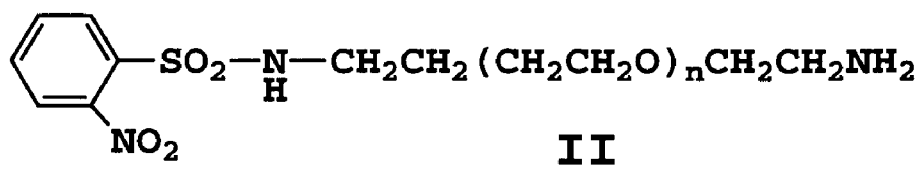
Figure 1A:
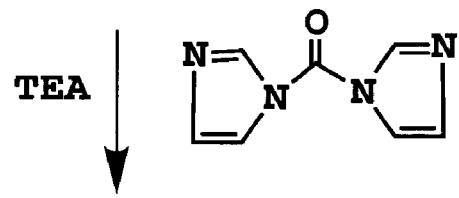
Figure 1A:
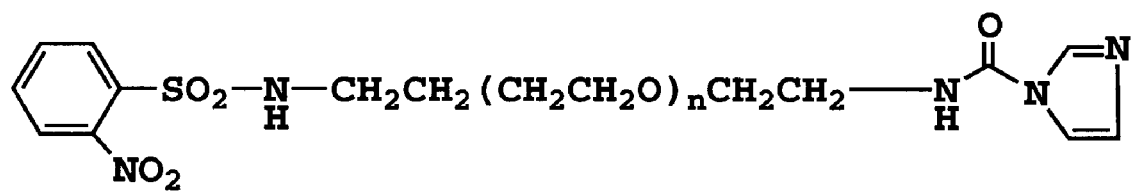
Figure 1A:
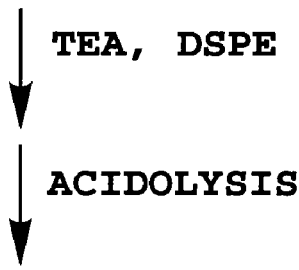

Unless otherwise indicated, the terms below have the following meaning:

"Vesicle-forming lipid" refers to any lipid capable of forming part of a stable micelle or liposome composition and typically including one or two hydrophobic acyl hydrocarbon chains or a steroid group and may contain a chemically reactive group, such as an amine, acid, ester, aldehyde or alcohol, at its polar head group.

"Effector" refers to polypeptides, mono or polysaccharides, and glycopeptides. Polypeptides, polysaccharides or glycopeptides may have sizes up to about 50–60 Kdaltons.

II. Effector Composition

The invention includes, in one aspect, a liposome composition for use in treating a subject with a small polypeptide or polysaccharide effector molecule which is effective as a pharmacological agent when circulating in free form in the bloodstream, but which is rapidly removed from the bloodstream by renal clearance. The composition includes a liposomal carrier composed of liposomes having an outer surface layer formed of hydrophilic polymer chains, e.g., PEG. The effector is attached to the distal ends of the polymer chains in at least a portion of the derivatized vesicle-forming lipid. The effector is attached to the distal end of a polymer chain to preserve the biological activity of the effector, such as behaving as a member of a ligand-receptor binding pair. The preparation of the composition follows the general procedures below.

A. Lipid Components

The liposomal carrier of the composition is composed of three general types of vesicle-forming lipid components. The first includes vesicle-forming lipids which will form the bulk of the vesicle structure in the liposome.

Generally, these vesicle-forming lipids include any amphipathic lipids having hydrophobic and polar head group moieties. Such a vesicle-forming lipid for use in the present invention is one which (a) can form spontaneously into bilayer vesicles in water, as exemplified by the phospholipids, or (b) is stably incorporated into lipid bilayers, with its hydrophobic moiety in contact with the interior, hydrophobic region of the bilayer membrane, and its polar head group moiety oriented toward the exterior, polar surface of the membrane.

The vesicle-forming lipids of this type are preferably ones having two hydrocarbon chains, typically acyl chains, and a polar head group. Included in this class are the phospholipids, such as phosphatidylcholine (PC), phosphatidylethanolamine (PE), phosphatidic acid (PA), phosphatidylinositol (PI), and sphingomyelin (SM), where the two hydrocarbon chains are typically between about 14–22 carbon atoms in length, and have varying degrees of unsaturation. The above-described lipids and phospholipids whose acyl chains have varying degrees of saturation can be obtained commercially or prepared according to published methods. Other suitable lipids include glycolipids and sterols such as cholesterol.

The second general component includes a vesicle-forming lipid which is derivatized with a polymer chain. Vesicle-forming lipids for use as the second general vesicle-forming lipid component (e.g., are suitable for derivatization with a polymer) are any of those described for the first general vesicle-forming lipid component. Vesicle forming lipids with diacyl chains, such as phospholipids, are preferred. One exemplary phospholipid is phosphatidylethanolamine (PE), which provides a reactive amino group which is convenient for coupling to the activated polymers. An exemplary PE is distearyl PE (DSPE).

A preferred polymer for use in forming the derivatized lipid component is polyethyleneglycol (PEG), preferably a PEG chain having a molecular weight between 1,000–10,000 daltons, more preferably between 2,000 and 5,000 daltons. Other hydrophilic polymers which may be suitable include polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses, such as hydroxymethylcellulose or hydroxyethylcellulose.

Additionally, block copolymers or random copolymers of these polymers, particularly including PEG segments, may be suitable. Methods for preparing lipids derivatized with hydrophilic polymers, such as PEG, are well known e.g., as described in co-owned U.S. Pat. No. 5,013,556.

The third general vesicle-forming lipid component is a lipid anchor by which the effector is anchored to the liposomes, through a polymer chain in the anchor. Additionally, the effector is positioned at the distal end of the polymer chain in such a way so that the biological activity of the effector is not lost. The lipid anchor has a hydrophobic moiety which serves to anchor the lipid in the outer layer of the liposome bilayer surface, a polar head group to which the interior end of the polymer is covalently attached, and a free (exterior) polymer end which is or can be activated for covalent coupling to the effector. Methods for preparing lipid anchor molecules of this types are described below.

B. Liposome Preparation

The liposomes may be prepared by a variety of techniques, such as those detailed in Szoka, F., Jr., et al., *Ann. Rev. Biophys. Bioeng.* 9:467 (1980). Multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

The lipid components used in forming the liposomes are preferably present in a molar ratio of about 70–90 percent vesicle forming lipids, 1–25 percent polymer derivatized lipid, and 0.1–5 percent lipid anchor. One exemplary formulation includes 50–70 mole percent underivatized PE, 20–40 mole percent cholesterol, 0.1–1 mole percent of a PE-PEG (3500) polymer with a chemically reactive group at its free end for effector coupling, 5–10 mole percent PE derivatized with PEG 3500 polymer chains, and 1 mole percent α-tocopherol.

The liposomes are preferably prepared to have substantially homogeneous sizes in a selected size range, typically between about 0.03 to 0.5 microns. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin, F. J., in *SPECIALIZED DRUG DELIVERY SYSTEMS-MANUFACTURING AND PRODUCTION TECHNOLOGY*, (P. Tyle, Ed.) Marcel Dekker, New York, pp. 267–316 (1990)).

C. Effector Component

The effector in the composition is a therapeutic polypeptide, mono or polysaccharide, or glycopeptide characterized, when administered intravenously in free form, by rapid clearance from the bloodstream, typically within 1–2 hours. The effector itself is effective as a pharmacological agent when circulating in free form in the bloodstream. Below are described preferred effectors for use in the invention.

1. $F_{ab}$ Fragment. The $F_{ab}$ fragment is one which has neutralizing activity against a given pathogen. The composition is used as a passive vaccine effective to provide humoral immunity against one of a variety of selected pathogenic antigens.

$F_{ab}$ fragments of neutralizing antibodies can be prepared according to conventional methods (Harlow, E., et al., in *ANTIBODIES: A LABORATORY MANUAL*, Cold Spring Harbor Press, Plainville, N.Y., (1988)). The fragment is preferably from a humanized monoclonal antibody ($M_{ab}$). Such antibodies can be prepared by published recombinant DNA methods (Larrick, J. W., et al., *Methods in Immunology* 2:106 (1991)). The antibody is preferably coupled to liposomal hydrophilic polymer groups via sulfhydryl linkages, as described above.

2. CD4 Glycoprotein Effector. The CD4 glycopeptide is a region of the CD4 receptor of CD4+ T cells (Capon and Ward). The effector acts to block HIV infection of CD4+ T cells by blocking gp120-mediated HIV binding to the CD4 receptor. The effector can be produced according to known recombinant methods (Maniatis, T., et al., in *MOLECULAR CLONING: A LABORATORY MANUAL*, Cold Spring Harbor Laboratory Press, Cold Spring Harbor, N.Y. (1989)).

3. Cytokines. The cytokines given in Table 1 below are examples of cytokines which are useful in the present invention. The cytokines may be obtained by recombinant production methods, according to published procedures. The therapeutic uses of the individual cytokines have been described in the literature (see, for example, Abbas, A. K., et al., in *CELLULAR AND MOLECULAR IMMUNOLOGY*, W.B. Saunders Company Harcourt Brace Jovanovich, Philadelphia (1991)). Some cytokine effectors may be administered on a short term basis to enhance a weak immunogenic or weak microbicidal response. The effectors may be administered on a long term basis as part of a therapy treatment for cancer or AIDS (Waldmann).

TABLE 1

| CYTOKINE | POLYPEPTIDE SIZE |
|---|---|
| A. Mediators of Natural Immunity | |
| IFN-alpha | 18 kD (monomer) |
| IFN-beta | 20 kD (monomer) |
| Tumor necrosis factor (TNF) | 17 kD (homotrimer) |
| Interleukin-1 (alpha and beta) | 17 kD (monomer) |
| Interleukin-6 | 26 kD (monomer) |
| Interleukin-8's | 8–10 (monomer or dimer) |
| B. Mediators of Lymphocyte Activation, Growth and Differentiation | |
| Interleukin-2 | 14–17 kD (monomer) |
| Interleukin-4 | 20 kD (monomer) |
| Transforming growth factor (beta) | 14 kD (monomer or dimer) |
| C. Mediators of Effector Cell Adhesion | |
| Gamma Interferon | 21–24 kD (homodimer) |
| Lymphotoxin | 24 kD (homotrimer) |
| Interleukin-5 | 20 kD (monomer) |
| D. Mediators of Immature Leukocyte Growth and Differentiation | |
| Interleukin-3 | 20–26 kD (monomer) |
| Granulocyte-macrophage Colony Stimulating Factor | 22 kD (monomer) |
| Macrophage Colony Stimulating Factor | 40 kD (dimer) |
| Granulocyte CSF | 19 kD (monomer) |
| Interleukin-7 | 25 kD (monomer) |

4. ELAM-1 Binding Inhibitor. Inflammation causes the expression of a polypeptide, endothelial leukocyte adhesion molecule-1 (ELAM-1), on the surface of endothelial cells of blood vessels, adjacent to sites of inflammation. ELAM-1, in turn, recognizes and binds a polysaccharide moiety, sialyl Lewis$^x$, on surfaces of neutrophils and recruits neutrophils to sites of inflammation. By preventing the recognition and binding of neutrophils by ELAM-1, excessive inflammatory responses due to conditions such as reperfusion injury, septic shock, and chronic inflammatory diseases, can be avoided.

In this embodiment, the effector is the tetrasaccharide, sialyl Lewis$^x$, recognized by ELAM-1 (Phillips, M. L., et al., *Science* 250:1130–1132 (1990)), for therapeutical use in preventing excessive recruitment of neutrophils to sites of inflammation in the blood stream. The effector is produced by the glycosylation mutants of Chinese hamster ovary (CHO) cells, and may be obtained in purified form from the cultured cells (Phillips). Alternatively, the effector is produced by chemical and/or enzymatic synthesis (Borman, S., *Chem. Eng. News*, December 7:25–28 (1992); Ichikawa, Y. et al., *J. Am. Chem. Soc.* 114:9283–9298 (1992)).

5. Inhibitors of IL-1 Activity. The effector in this embodiment is an IL-1 inhibitor, or IL-1 receptor antagonist (IL1RA), which blocks binding of IL-1 to receptors on lymphocyte cell surfaces (Stylianou, E., et al., *J. Biol. Chem.* 267:15836–15841 (1992)).

IL-1 production is stimulated by both endotoxins which cause septic shock and exotoxins which cause toxic shock syndrome (Dinarello, C. A., *Blood* 77(8):1627–1650 (1991)). IL-1 production during septic shock or toxic shock may exacerbate the clinical symptoms observed in patients. Therefore, use of an IL-1 inhibitor effector to decrease the clinical symptoms associated with either toxic shock or septic shock may be beneficial.

IL-1 inhibitor is a 52 to 66 Kd polypeptide that binds specifically to IL-1 to inhibit its immunostimulatory responses. IL1RA is a 23 to 25 KD polypeptide that competes with binding of IL-1 to its cell surface receptors to inhibit IL-1's immunostimulatory responses.

6. Polymyxin B. This effector is a cationic detergent with a hydrophobic portion (6-methyloctanoyl) and a short basic decapeptide portion. Polymyxin B reacts with and neutralizes gram-negative bacterial endotoxins, specifically *E. coli* 0111:B4 liposaccharide (LPS) (Baldwin, et al.). Polymyxin B is used in the treatment of gram-negative bacterial infections. Since polymyxin B must be administered frequently and in high doses because of its rapid clearance from the bloodstream, it causes severe irreversible kidney damage. Polymyxin B can be chemically synthesized or isolated from spore-forming gram-positive bacilli, such as *Bacillus polymyxa*.

Alternatively, the effector is an 11.8 Kdalton peptide isolated from amebocytes of *Limulus polyphemus*, limulus antilipopolysaccharide factor (LALF). LALF neutralizes meningococcal lipooligosaccharide, as well as other gram-negative endotoxins, and can be used to treat gram-negative sepsis (Wainright, N. R., et al., In *CELLULAR AND MOLECULAR ASPECTS OF ENDOTOXIN REACTIONS* (Nowotny, A., et al., Eds.) Elsevier Science Publishers B. V., p. 315 (1990)).

7. Peptide Hormone. This effector can be used in the treatment of various diseases. In one embodiment, the effector is parathyroid hormone (PTH) which is 84 amino acids in length and can inhibit osteoblast division. Certain bone cancers are characterized by uncontrolled osteoblast division (Kano, J., et al., *Biochem. Biophys. Res. Comm.* 179:97–101 (1991)). Alternatively, the peptide hormone can be used to target a liposome to cells that contain receptors for a specific peptide hormone.

D. Attachment of Effector to Liposome Carrier

For effector attachment to liposome carriers, the free polymer end of a lipid anchor is activated prior to effector coupling. In the following specific examples, both lipid anchor formation and activation reactions are described. The reactions are shown with respect to the free lipid, either distearylphosphatidyl-ethanolamine (DSPE) or PE.

The activated lipid anchors are then incorporated into liposomal carriers, as described above.

One advantage of activating the PEG terminal group of the lipid anchor prior to liposome formation is that a broader range of reaction solvents and reaction conditions may be employed. Further, the liposomes themselves are not exposed to the activating reagents. Thus, the need to remove reagent contaminants from the liposomes is avoided.

It will also be appreciated that the activation reactions may be performed after lipid anchor incorporation into liposomal carriers. In some coupling reactions it may be more desirable to activate the terminal PEG groups on preformed liposomes. One advantage of this approach is that the activation reaction is confined to the outer, surface-accessible lipids, and thus the activated groups can be completely quenched prior to use of the composition in therapy. The approach is also preferred for reactions in which the activated PEG termini are unstable in water.

Figure 1B:
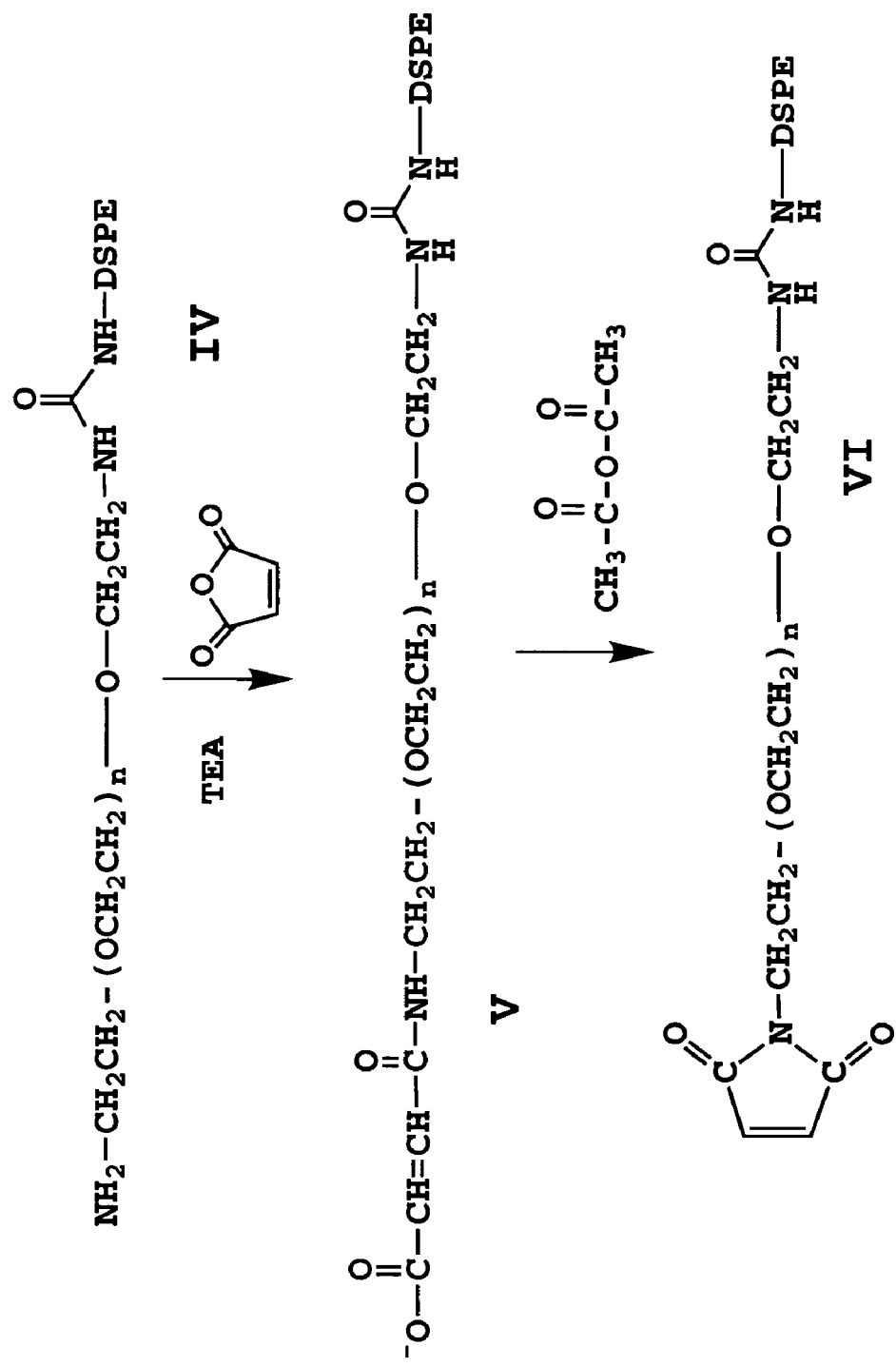

FIGS. 1A–1B show the synthesis of DSPE derivatized with a PEG chain and having an activated maleimide group at the chain's free end. Initially, PEG bis (amine) (compound I) is reacted with 2-nitrobenzene sulfonyl chloride to generate the monoprotected product (compound II). Compound II is reacted with carbonyl diimidazole in triethylamine (TEA) to form the imidazole carbamide (e.g., urea) of the mono 2-nitrobenzenesulfonamide (compound III).

Compound III is reacted with DSPE in TEA to form the derivatized PE lipid protected at one end with 2-nitrobenzyl sulfonyl chloride. The protecting group is removed by treatment with acid to give the DSPE-PEG product (compound IV) having a terminal amine on the PEG chain. Reaction with maleic anhydride gives the corresponding end-functionalized product (compound V), which on reaction with acetic anhydride gives the desired DSPE-PEG-maleimide product (compound VI). Details of the reactions are given in Example 1.

Figure 9:
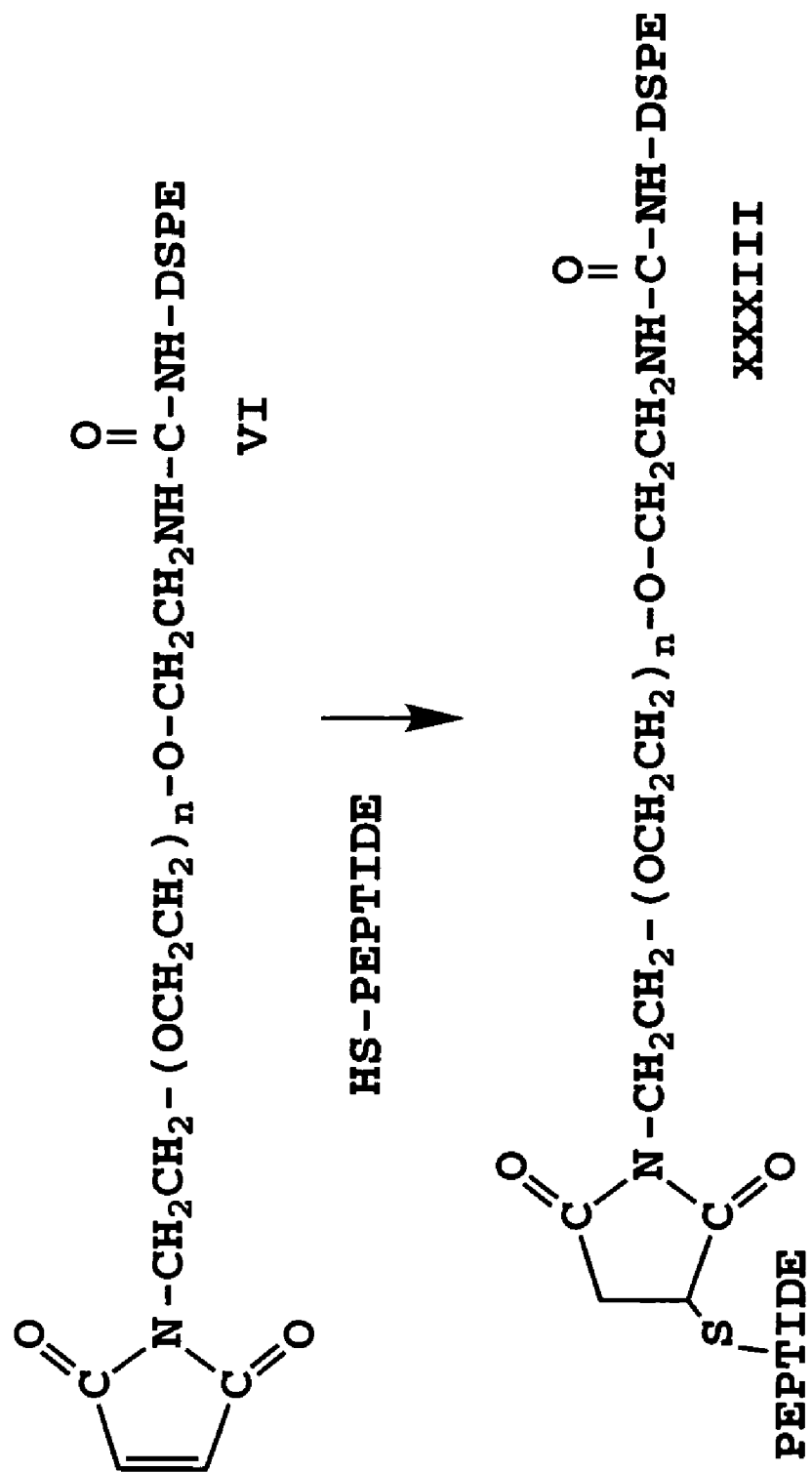
FIG. 9 shows the covalent coupling of a sulfhydryl-containing peptide to the terminal maleimide group of a DSPE carbamide PEG derivative.

The compound is reactive with sulfhydryl groups, for coupling polypeptides through a thioether linkage, as illustrated in FIG. 9.

Figure 2:
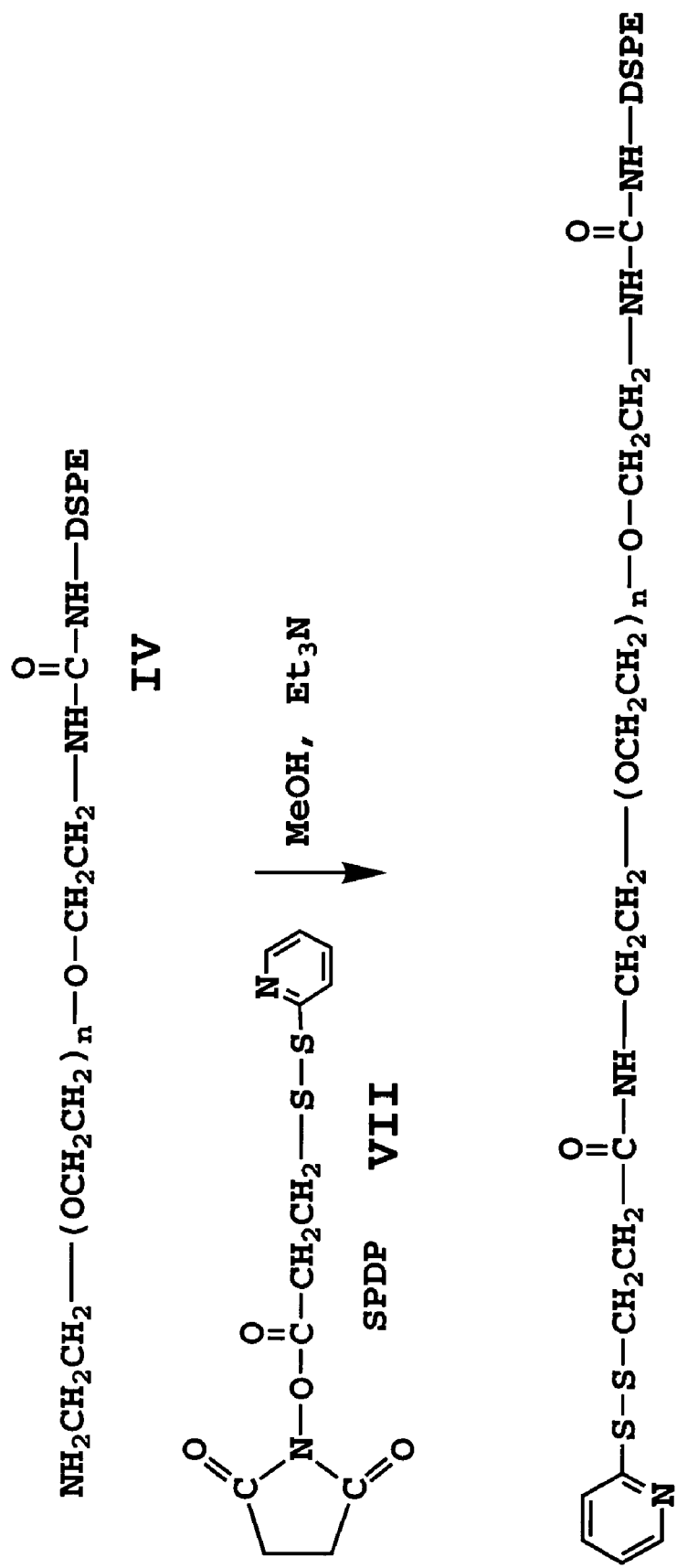
FIG. 2 shows steps for the synthesis of a disulfide linkage-containing propionamide of a DSPE (distearyl phosphatidylethanolamine) carbamide of polyethylene glycol (PEG) bis (amine)
Figures 10, 11:
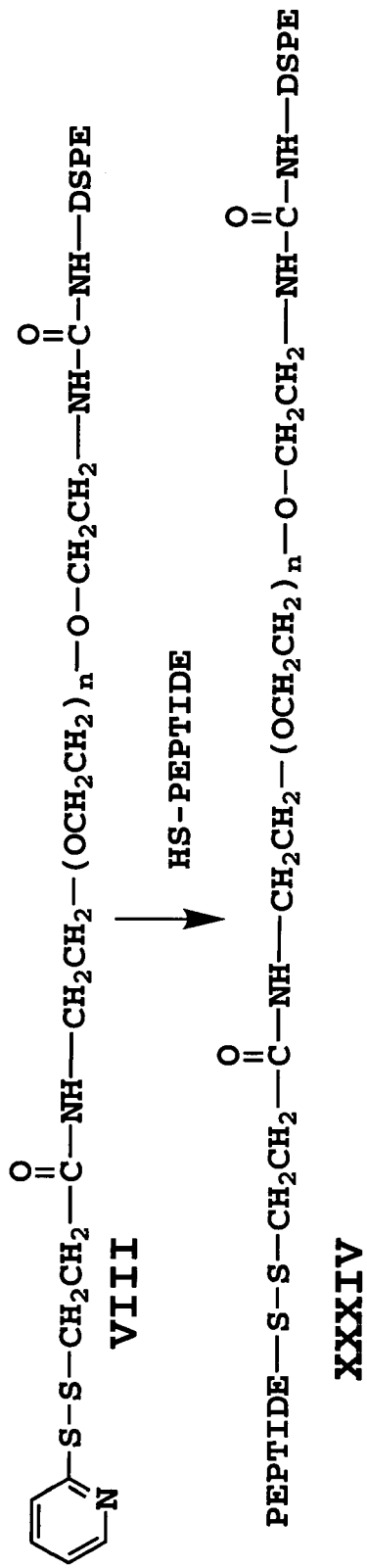
FIG. 10 shows the covalent coupling of a sulfhydryl-containing peptide via formation of a disulfide bond to a DSPE carbamide of a terminally functionalized PEG containing a reactive disulfide linkage derived from SPDP (N-succinimidyl 3-(2-pyridyldithio)-propionate)
FIG. 11 shows the covalent coupling of a peptide through the aldehyde group of an ethylene-linked derivative of DSPE carbamide of PEG by reductive amination.

FIG. 2 illustrates an exemplary synthesis of another derivatized lipid useful for coupling to sulfhydryl-containing polypeptides. Here the DSPE-PEG lipid (compound IV) described above is treated with N-succinimidyl-3-(2-pyridyldithio) propionamide, SPDP, (compound VII) to form the anchor DSPE-PEG lipid (compound VIII). The compound can, for example, react with a sulfhydryl group of a peptide to thereby couple the peptide to the lipid through a disulfide linkage as illustrated in FIG. 10.

Figure 3:
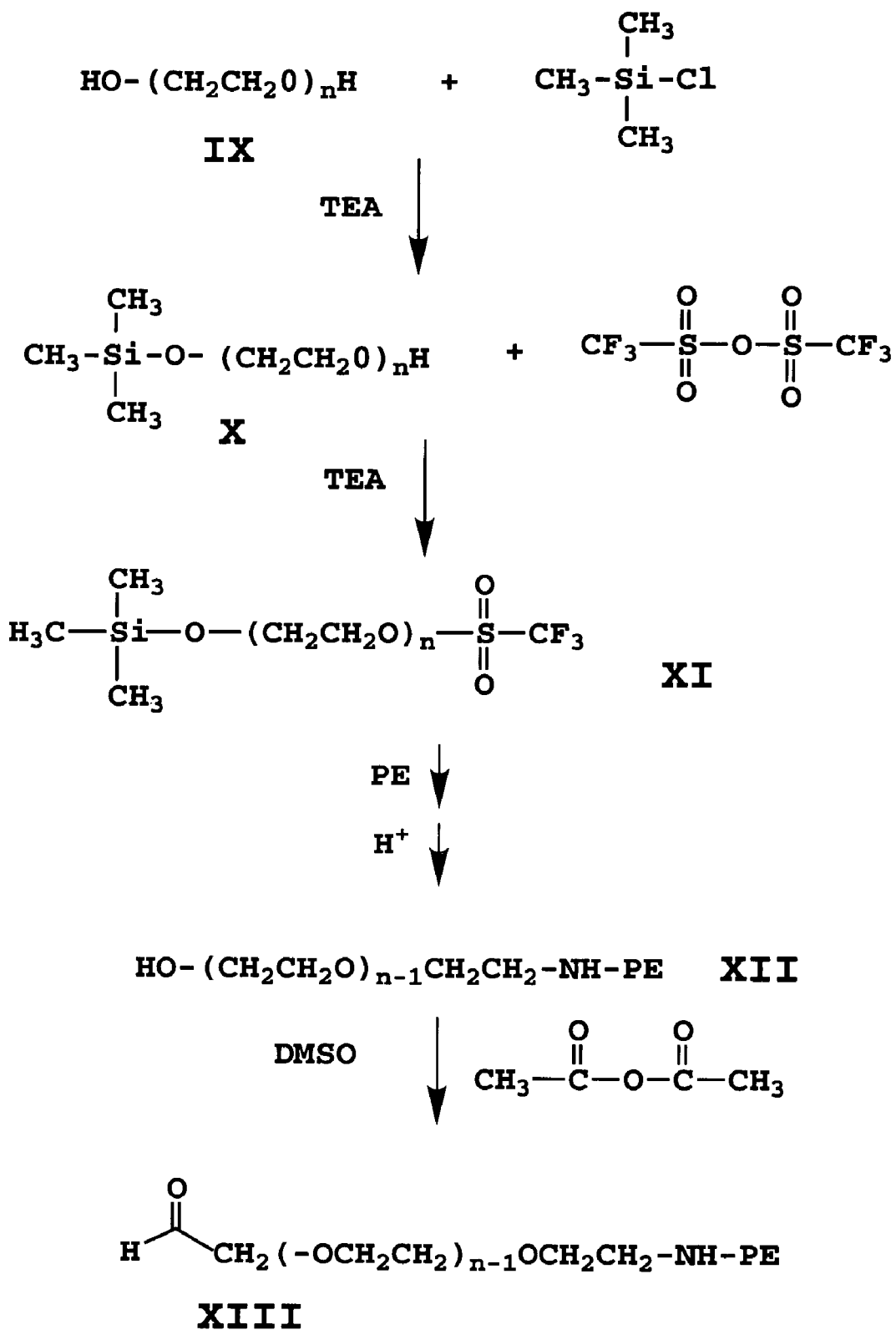
FIG. 3 shows a synthetic scheme for the preparation of a PEG-derivatized PE (phosphatidylethanolamine) containing a terminal aldehyde group.

Another synthetic approach for coupling a protected polyalkylether to a lipid amine is shown in FIG. 3. In this reaction scheme, PEG (compound IX) is initially protected at one of its terminal OH ends by a trimethylsilyl group, as shown at the top of FIG. 3. The monoprotected PEG (compound X) is reacted with the anhydride of trifluoromethyl sulfonate to activate the free PEG end with trifluoromethyl sulfonate (compound XI). Reaction of the activated PEG compound with a lipid amine, such as PE, in the presence of triethylamine, and release of the trimethylsilyl protecting group by acid treatment, gives the PE-PEG derivative (compound XII). This compound contains a terminal alcohol group which is then oxidized in the presence of dimethylsulfoxide (DMSO) and acetic anhydride to form an aldehyde group (compound XIII) which can be coupled to a peptide via reductive amination, as illustrated in FIG. 11. Reaction details are given in Example 2.

More generally, the derivatized lipid components can be prepared to include a lipid-polymer linkage, such as a peptide, ester, or disulfide linkage, which can be cleaved under selective physiological conditions, such as in the presence of peptidase or esterase enzymes or reducing agents, such as glutathione, present intracellularly.

Figure 4:
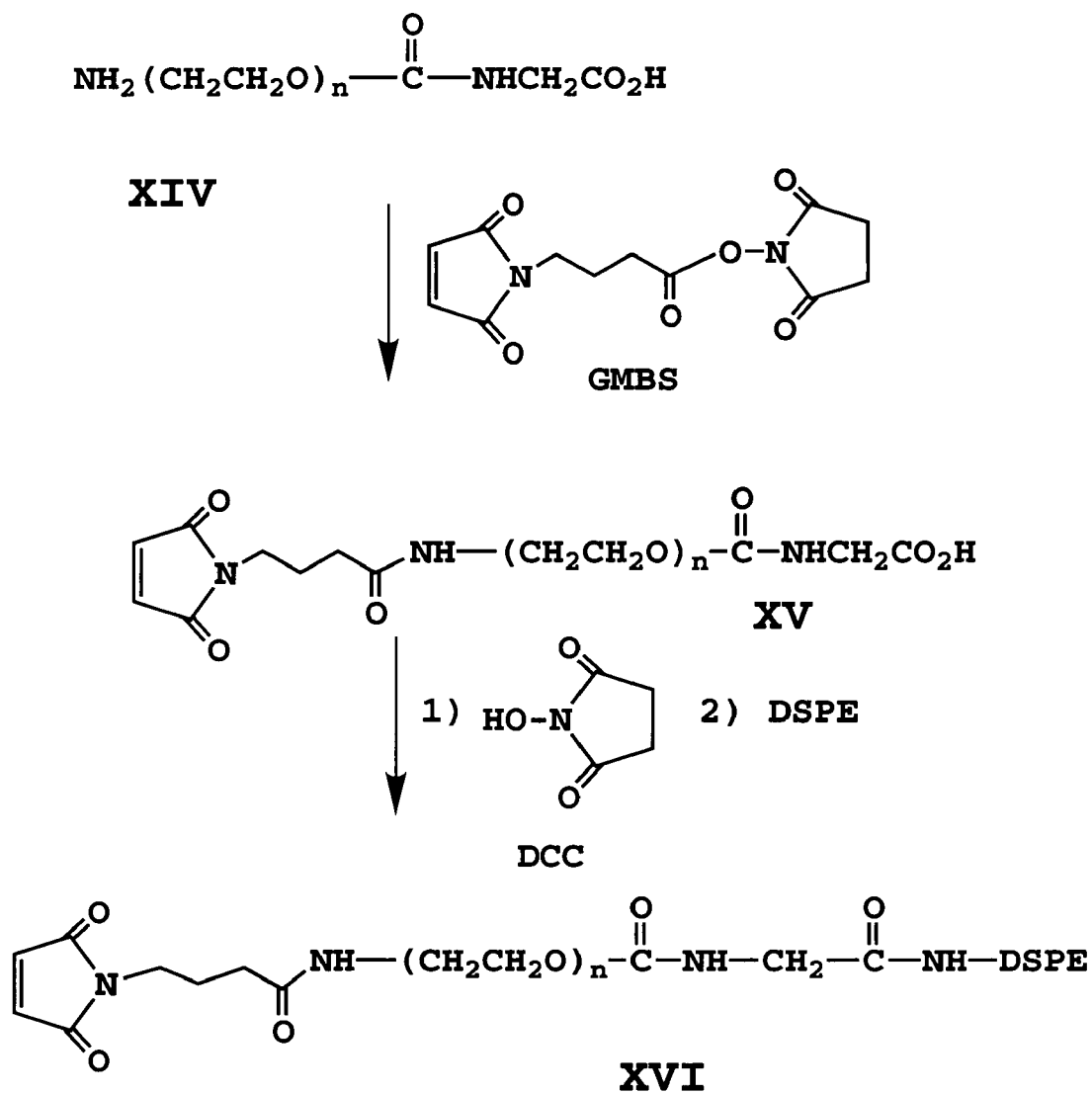
FIG. 4 illustrates a synthetic scheme for forming a PEG-derivatized DSPE having a reactive maleimide group at the PEG terminus.

An alternative general method for preparing lipid derivatives of PEG suitable for coupling to effector molecules involves using α-amino-ω-carboxy derivatives of PEG (such as compound XIV) as starting materials. This alternative approach is illustrated in FIGS. 4, 5, and 6.

Methods for preparing heterobifunctional PEG derivatives such as compound XIV have been described by Zalipsky, S., et al., *Polymer Preprints* 27(1):1 (1986); Zalipsky, S., et al., *J. Bioactive Compat. Polym.* 5:227 (1990)). In the reaction scheme shown in FIG. 4, an α-amino-ω-carboxy functionalized PEG (Zalipsky, et al., 1986) is reacted with N-(γ-maleimidobutyryl-oxy)succinimide ester (GMBS, Pierce), using an excess of GMBS. The terminal carboxyl group of the resulting maleimido-PEG (compound XV) is then reacted with a lipid amine, such as PE or DSPE, in the presence of N-hydroxysuccinimide, to link the PEG to the lipid through an amide linkage (compound XVI). The maleimido group at the "free" end of the polymer is reactive towards thiol-containing ligands, proteins, e.g., immunoglobulins and fragments thereof.

Figure 5:
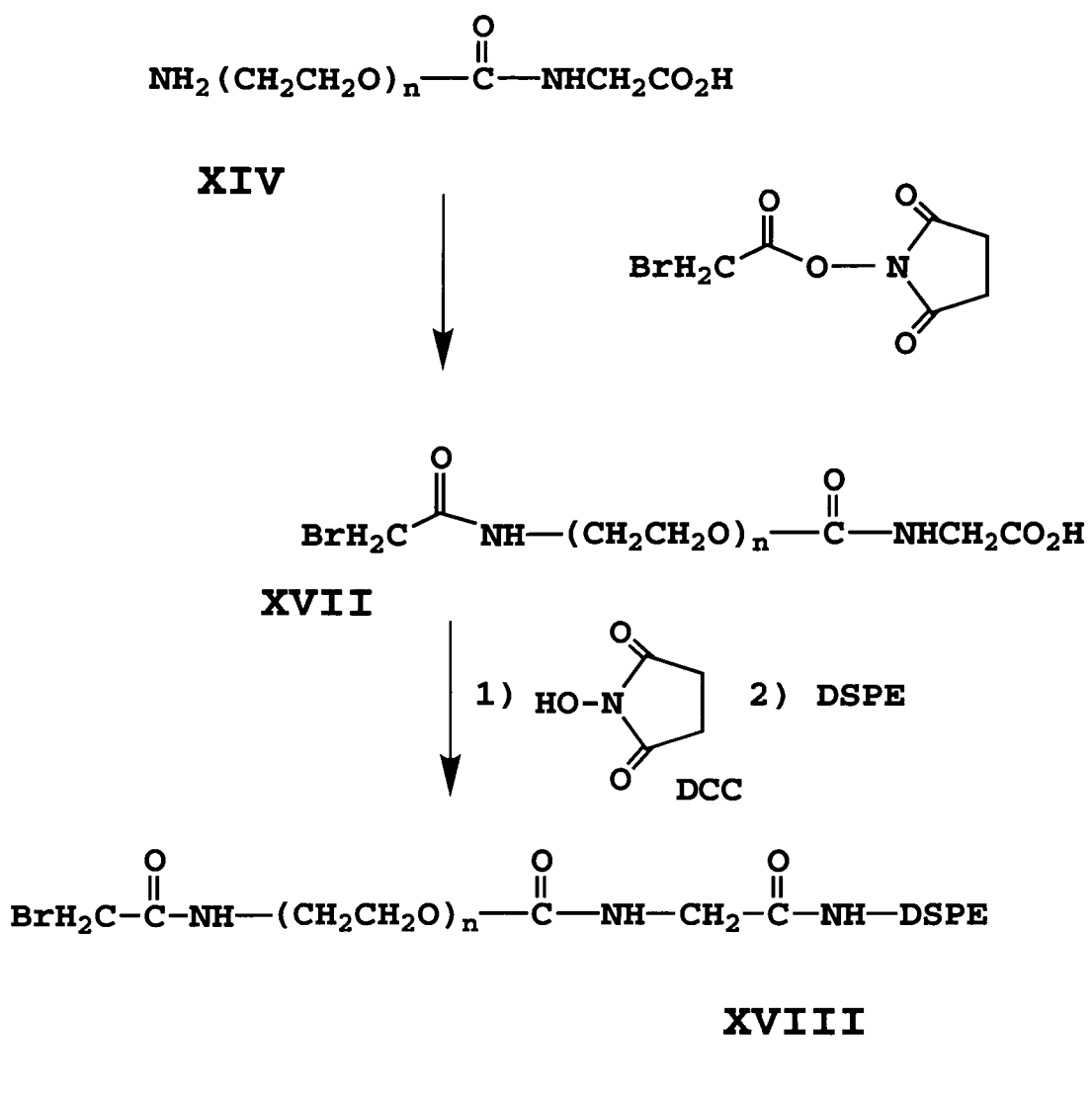
FIG. 5 illustrates an exemplary method for forming a PEG-derivatized DSPE containing a bromoacetamide group at the polymer end.

A related scheme is illustrated in FIG. 5, which shows introduction of a terminal bromoacetamide group in an α-amino-ω-carboxy-functionalized PEG. In the approach shown, a derivative of PEG is reacted with bromoacetyl N-hydroxysuccinimide ester. The bromoacetamido-functionalized PEG is then coupled to a suitable lipid amine, such as PE or DSPE, as above, to form the derivatized lipid (compound XVIII). The bromoacetamide group, being more selective and more stable than a maleimide group, allows greater flexibility in the methods used for liposome formation and loading.

Figure 6:
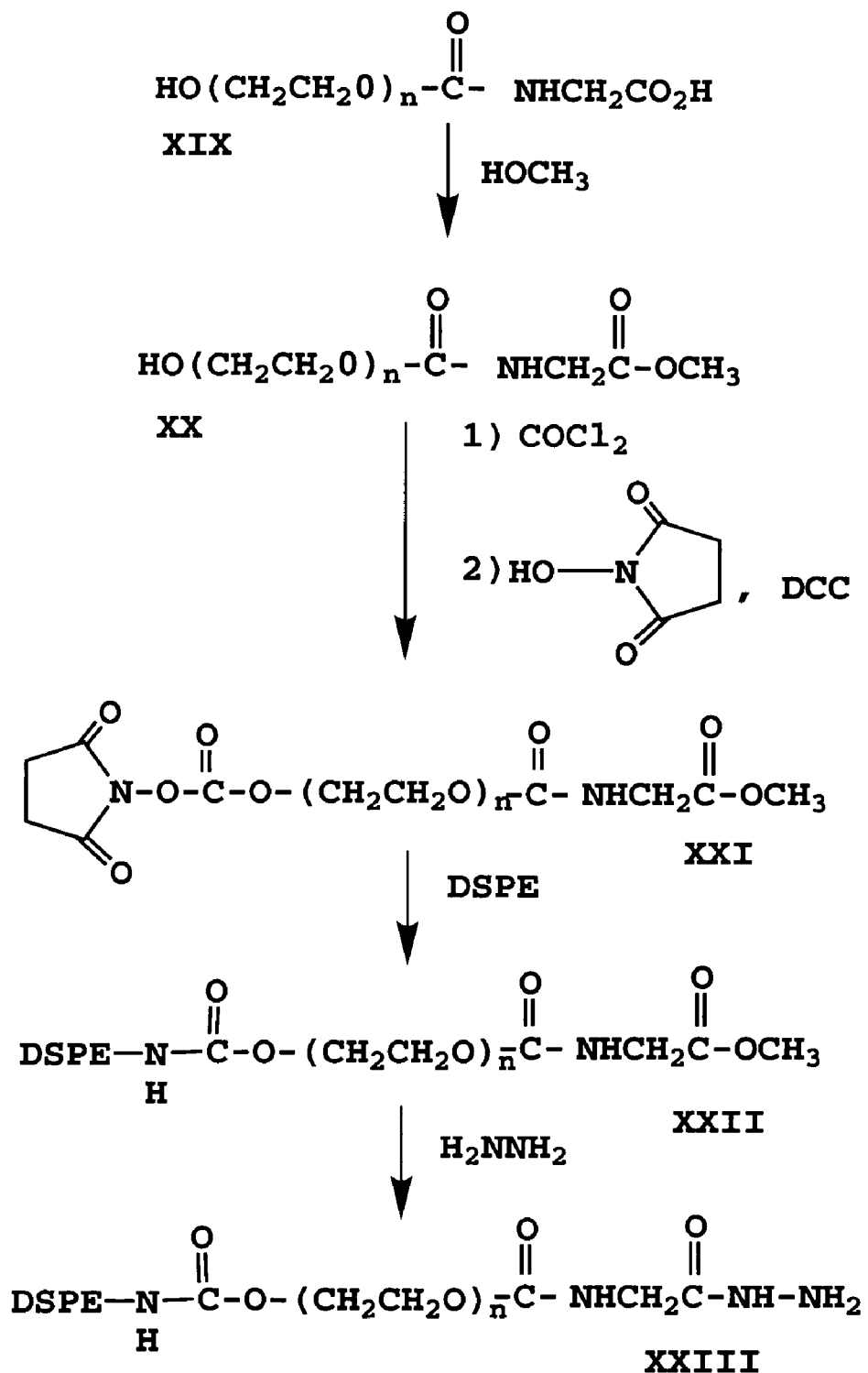
FIG. 6 shows an exemplary method for synthesizing a derivatized DSPE lipid with a PEG chain functionalized to contain a terminal hydrazide group.

The reaction scheme shown in FIG. 6 illustrates the preparation of a derivatized lipid in which the free PEG end is functionalized to contain a hydrazide. In the reaction illustrated in FIG. 6, an α-hydroxy-ω-carboxylic acid PEG derivative (compound XIX) (Zalipsky, et al., 1990) is esterified with methanol to protect the terminal acid group by formation of the corresponding ester (compound XX). The terminal hydroxyl group is then converted into a functional group reactive towards primary amines (Zalipsky, S., et al., in *POLY (ETHYLENE GLYCOL) CHEMISTRY: BIOTECHNICAL AND BIOMEDICAL APPLICATIONS* (J. M. Harris, Ed.) Plenum Press, pg. 347–370 (1992a)), for example, a succinimidyl carbonate (SC) derivative (compound XXI). This compound is formed, for example, by reacting compound XX with phosgene followed by subsequent reaction with N-hydroxysuccinimide (Zalipsky, S., et al., *Biotechnol. Appl. Biochem.* 15:100 (1992b)). The resulting activated PEG compound, SC-PEG-C(O)NHCH$_2$CO$_2$—Me (compound XXI) reacts with a lipid amine such as PE or DSPE at the reactive succinimidyl carbonate group to form the functionalized lipid, DSPE-PEG-C(O)NHCH$_2$CO$_2$-Me (compound XXII). The methyl ester can be readily hydrazinolyzed to yield DSPE-NHCO$_2$—PEG-C(O)NHCH$_2$C(O)—N$_2$H$_3$ (compound XXIII), as shown. This hydrazide-containing PEG-lipid is incorporated into liposomes by conventional methods. The hydrazide group can be used for attachment of aldehyde or ketone containing effector molecules.

Such carbonyl groups exist or can be easily generated on numerous carbohydrate containing molecules, e.g. oligosaccharides, nucleotides, low molecular weight glycosides, lectins, immunoglobulins and other glycoproteins by chemical (periodate oxidation) or enzymatic reactions (galactose oxidase). The linkages formed, hydrazones, are reasonably stable at pH$\geq$7.5, but are cleavable by acid catalyzed hydrolysis at lower pH values. These linkages can be stabilized by reduction, e.g., with sodium cyanoborohydride. An advantage of this approach is the stability of hydrazide groups which allows the use of a wide array of liposome formulations and loading protocols.

Figure 7A:
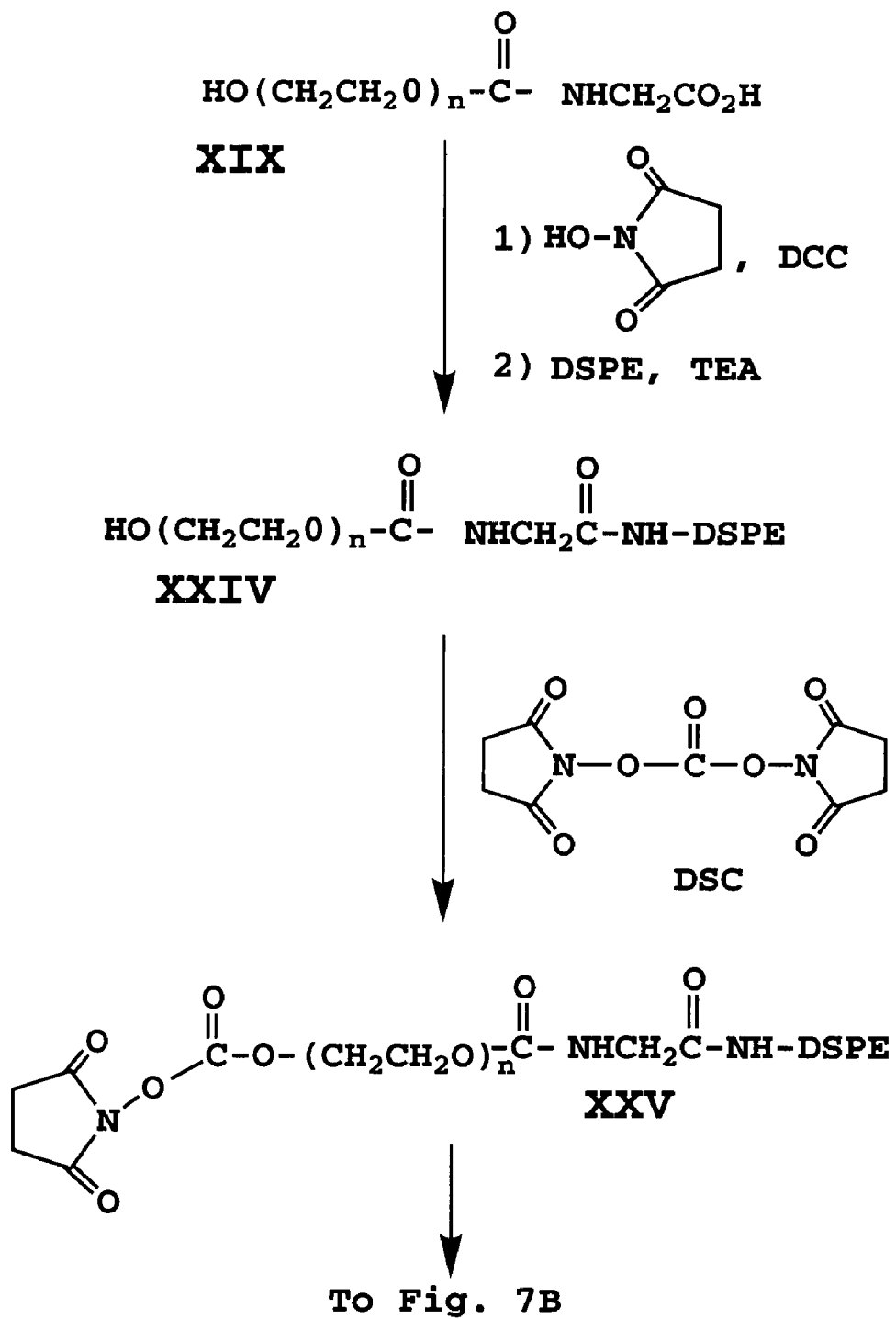
FIGS. 7A–7D show steps in the synthesis of a PEG-derivatized DSPE lipid containing a reactive group at the polymer end (FIG. 7A) which can be used to couple to a variety of amine containing groups (7B–7D)

Alternatively, as illustrated in FIG. 7A, an α-hydroxy-ω-carboxy derivative of PEG (compound XIX) can be coupled to a lipid containing a terminal amino group, e.g., DSPE, by reaction with N-hydroxysuccinimide in the presence of a coupling agent such as dicyclohexylcarbodiimide, DCC. The resulting intermediate, the N-hydroxysuccinimide (NHS) ester of α-hydroxy-PEG, is then suitable for coupling to an amino-end containing lipid such as DSPE by displacement of the NHS group to form a α-hydroxy-PEG-DSPE conjugate, linked by an amide bond (compound XXIV, FIG. 7A). The α-hydroxy group of PEG can then be further activated, such as by reaction with disuccinimidyl carbonate (DSC), to form an α-succinimidyl carbonate-PEG-DSPE compound (compound XXV) suitable for coupling to a variety of compounds containing reactive amino groups.

Preparation of compound XXIV is described in Example 4. Amino-group containing compounds for coupling to such functionalized lipids will also possess at least one other functional group to which effector molecules may be attached. The attachment of the effector molecules may occur before or after liposome formation.

Figure 7B:
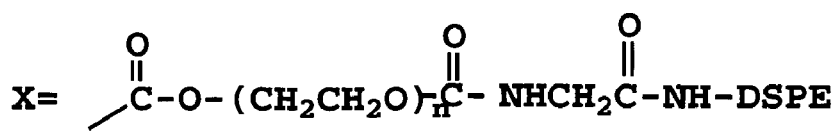
Figure 7B:
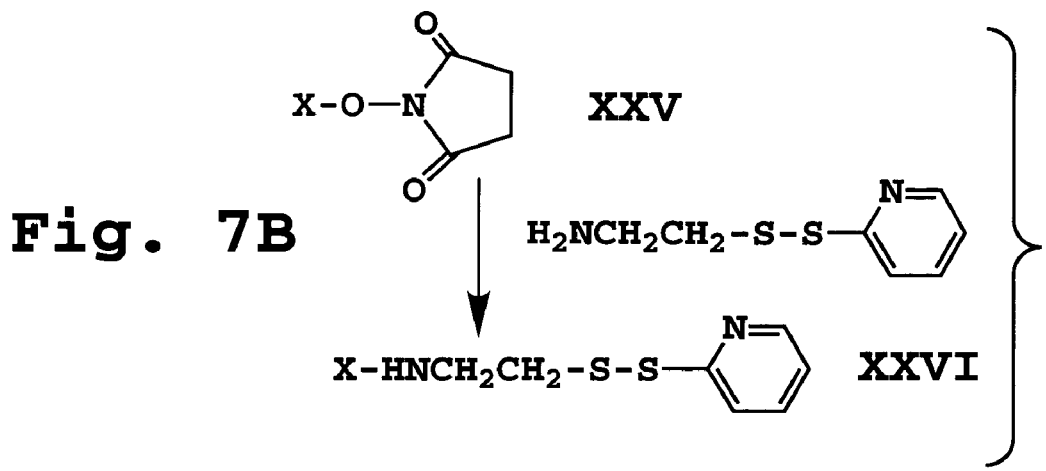

In one case, as illustrated in FIG. 7B, the SC-PEG-DSPE is reacted with 2-aminoethanedithiopyridine. The derivative formed (compound XXVI) can be used in the following manner. The dithiopyridine group is reactive towards thiol-containing molecules but is also quite stable under a variety of conditions. Using mild reducing agents, e.g., β-mercaptoethanol, it is possible to convert the dithiopyridine groups on the liposomes into free thiols, which in turn can be used in various conjugation procedures involving ligands containing reactive maleimido or bromoacetate groups or reactive mixed disulfide groups such as dithiopyridine.

Figure 7C:
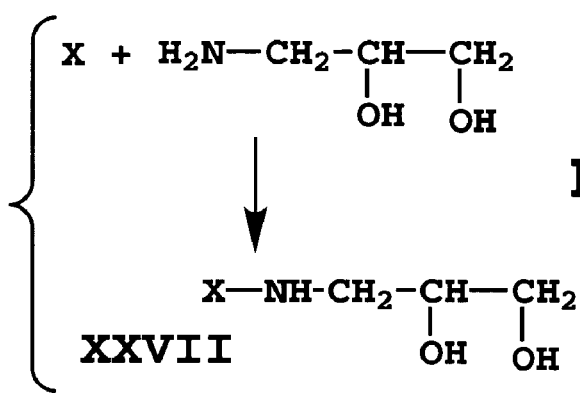

In the reaction illustrated in FIG. 7C, the SC-PEG-DSPE is reacted with 3-amino-1,2-propanediol, producing a diol terminated PEG-lipid (compound XXVII). After incorporation into a liposome, the diol can be oxidized (e.g., with periodate) under mild conditions ([I0$_4$-]$\leq$10 mM, 4° C.) to provide a reactive aldehyde. The aldehyde containing PEG-liposomes will react irreversibly with a variety of amino-containing effector molecules in the presence of a reducing agent such as sodium cyanoborohydride.

Figure 7D:
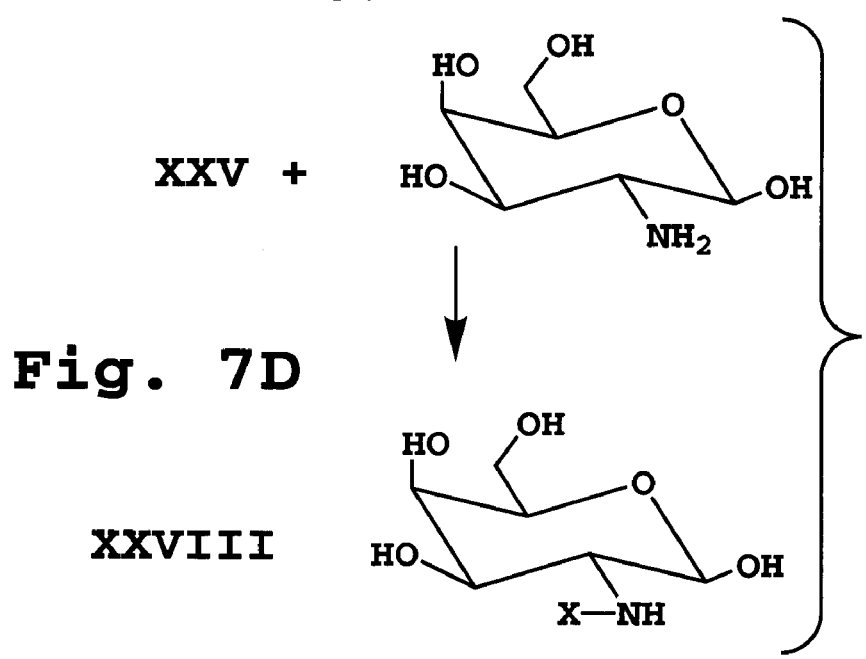

In the reaction illustrated in FIG. 7D, SC-PEG-DSPE is coupled to a galactosamine. The galactose residue on the derivatized lipid (compound XXVIII) can then be enzymatically oxidized by galactose oxidase. The aldehyde bearing PEG-liposomes obtained by this process can be used for conjugation with amino-group containing effector molecules. In addition to the mildness of the reaction conditions, the aldehyde groups are generated solely on the outer surface of the liposome.

Additionally, there is evidence that oxidized galactose residues are useful for stimulation of the immune system, specifically for T cell activation. A liposome having oxidized galactose residues on its surface is likely to act as an adjuvant and might be useful in vaccines (Zheng, B., et al., *Science* 256:1560–1563 (1992)).

Figure 8:
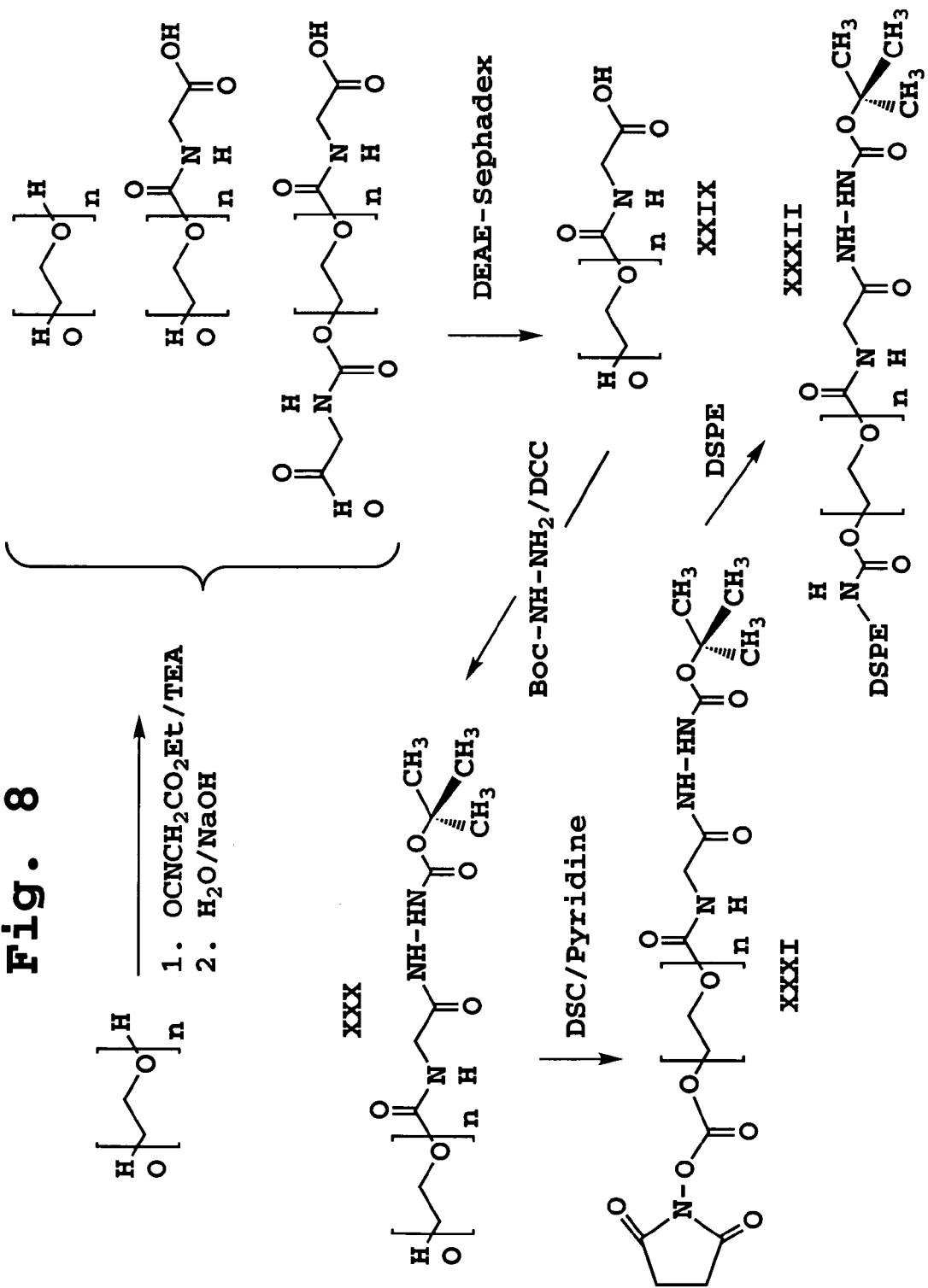
FIG. 8 shows one synthetic approach for forming DSPE derivatized by a PEG spacer chain having a terminal hydrazide group (shown in protected form)

In another procedure, illustrated in FIG. 8 and described in Example 5, DSPE-PEG-hydrazide is prepared. First PEG is reacted with ethyl isocyanatoacetate in the presence of triethylamine to generate mono and di-end carboxylated species of PEG, where the carboxylic acid functions are connected to the PEG skeleton via intervening carbamate bonds. The monocarboxylated species is purified by ion-exchange chromatography on DEAE-Sephadex (compound XXIX, identical to compound XIX). Compound XXIX is reacted with tert-butyl carbazate to generate the ω-hydroxy-α-Boc-hydrazide derivative of PEG (compound XXX). The hydroxyl terminus of PEG is then activated by reaction with disuccinimidyl carbonate to form compound XXXI prior to reaction with DSPE to generate the desired lipid-PEG-α-Boc hydrazide product (compound XXXII). Compound XXXII is deprotected with 4M HCl in dioxane to form the free hydrazide group. Lipid-PEG-hydrazide may then be incorporated into liposomes. The hydrazide groups are reactive towards aldehydes, which as described above, can be generated on numerous biologically relevant compounds.

The methods just described may be applied to a variety of lipid amines, including PE, cholesteryl amine, and glycolipids with sugar amine groups. It will be appreciated that a variety of alternative coupling reactions, in addition to those just described, are suitable for preparing vesicle-forming lipids derivatized with hydrophilic polymers such as PEG, having terminal groups which are activated or are reactive in protein coupling reactions.

1. Maleimide Coupling. Maleimides are widely used protein modifying reagents and are especially useful when the maleimide is one of two functional groups in a heterobifunctional crosslinking reagent. The reaction of maleimides with sulfhydryl groups involves Michael addition of the mercaptan group to the activated double bond. Reaction with amino groups occurs by the same mechanism, but at a much slower rate. Since mercaptan is the most reactive species, particularly at neutral pH, the maleimide group can be used to target a small number of sulfhydryl groups and good selectivity is usually achieved.

In one preferred embodiment, a derivatized lipid, such as PE- or DSPE-PEG, is prepared to contain a terminal maleimide group (compounds VI and XVI), as illustrated in FIGS. 1 and 4 above. The lipid, after incorporation into liposomes, is then reacted with a sulfhydryl-containing effector, typically a polypeptide, under suitable coupling conditions. The reaction of the terminal maleimide-PEG lipid (compound VI or XVI) with a peptide sulfhydryl group is illustrated in FIG. 9. As shown, the reaction couples the protein to the lipid polymer through a thioether linkage, to give the derivatized DSPE (compound XXXIII). Use of this synthetic approach to couple proteins to liposomes is described in Example 6.

The efficiency of β-galactosidase coupling to liposomes containing a maleimide coupling agent in the presence or absence of DSPE-PEG3500 has been examined and the results are discussed below.

Reactions were carried out with liposomes prepared to contain, as the maleimide coupling agent, either (a) the DSPE derivative of succinimidyl 4-(p-maleimidophenyl) butyrate (MBP), (b) the DSPE derivative of N-(11-maleimido-undecanoyl) (C11), or (c) the maleimide of PE-PEG3500. Reactions carried out with (c) are described in detail in Example 6.

After carrying out the protein-liposome coupling reaction, performed as described above for (a)–(c), the amount of liposome-bound enzyme was quantitated. Recovery of liposomes was measured by scintillation counting and the recovery of protein was measured by the beta-galactosidase assay and direct quantitation of the protein amount as described in Example 6.

The maleimide of the DSPE carbamide of PEG3500 was very effective in crosslinking β-galactosidase to liposomes, either in the presence or absence of DSPE-PEG3500 chains. As seen in Table 2, there was essentially no difference in the amount of protein crosslinked to either type of liposome in two separate experiments. In addition, the amount of protein coupled to the PE-PEG maleimide was much higher than to either the MPB or MPB-$C_{11}$ maleimides.

The presence of "non-activated" DSPE-PEG3500 in the liposomes had little effect on the levels of coupling of the protein to DSPE-PEG-maleimide liposomes, but inhibited the level of protein coupling to liposomes containing either the MPB lipid, or the MBP-$C_{11}$ lipid.

TABLE 2

| Phenotype" | | | ng Protein/ |
|---|---|---|---|
| PEG-DSPE | Crosslinker | 10 mM 2-ME | µmol Lipid* |
| − | MPB | | 1609/2284 |
| − | MPB | + | (−80) |
| + | MPB | | (−282) |
| − | $C_{11}$ | | 690 |
| − | $C_{11}$ | + | 847 |
| + | $C_{11}$ | | 358 (−157) |
| + | $C_{11}$ | + | 80 |
| − | 3500 | | 10,033 |
| − | 3500 | + | 572 |
| + | 3500 | | 10,765/12,412 |
| + | 3500 | + | 110 |

*Background binding in the absence of crosslinker has been subtracted. Background values range from 500–1000 ng protein/µmol lipid. There was a tendency for background values to be somewhat (10–30%) higher in the presence of PEG-DSPE; this may not be significant. Multiple entries denote multiple separate crosslinking experiments.

2. Coupling by 3-(2-pyridyldithio) propionamide.

The reaction of dithio propionamides with a sulfhydryl group produces coupling of functionalized lipids to sulfhydryl-containing molecules via a disulfide linkage. Disulfide exchange occurs readily at pH 8, in a non-reducing environment. The method involves reaction of a thiol group in a peptide with a liposome prepared to contain DSPE-PEG-(2-pyridyldithio) propionamide). The reaction couples the protein to the liposomes through a disulfide linkage as illustrated in FIG. 10 (compound XXXIV).

3. Reductive Amination

In this approach, the terminal hydroxyl group of a PEG chain, covalently linked at one end to PE or DSPE, is converted to the corresponding aldehyde by oxidation under mild conditions. The oxidation step may be carried out before or after incorporation into liposomes to produce the aldehyde form of the derivatized lipid (compound XIII in FIG. 3). Reaction of the aldehyde with the amine group of an effector molecule gives the Schiff base (compound XXXV, FIG. 11) which is then reduced to the desired derivatized lipid containing an amino-linked peptide (XXXVI).

As indicated above, the polymers can also be activated for effector coupling in preformed lipids, i.e., with the polymer-derivatized lipids already incorporated into liposomes. One advantage of this approach is that only polymer moieties on the outer surface of the liposomes are activated. In one general approach involving PEG polymers, the terminal OH groups are first oxidized by treatment with sodium periodate for 2 hours at 20° C. in the dark. After oxidation, the excess reagent is removed, and the liposomes are incubated with the effector molecule, e.g. $F_{ab}$ fragments, in the presence of 2M sodium cyanoborohydride (10 µL/mL) at 20° C. for 14 hours. After completing the incubation, the liposomes can be chromatographed on a Sepharose to remove free (non-linked) effector molecules.

III. Bloodstream and Tissue Retention of Liposomes Containing End-Functionalized PEG-DSPE In vivo studies were undertaken to determine the bloodstream and tissue retention of liposomes containing end-functionalized PEG-DSPE, as described in Example 7. End-functionalized PEG-DSPE contains a chemically active group which can be used for attaching a variety of compounds to liposomes. From these studies it has been determined that end-functionalization does not affect the extended lifetime in the bloodstream of liposomes containing PEG-DSPE, monomethoxy PEG-DSPE, or other similarly modified vesicle-forming lipids.

In experiments performed in support of the present invention, liposomes containing PEG-DSPE end-functionalized by hydrazide were prepared. The hydrazide group at the end of a PEG chain can be used for the introduction of other functional groups, or can be used in numerous types of conjugation schemes (Inman, J. K., *Meth. Enzymol.* 34:30–58 (1974)). Particularly useful is hydrazide's reactivity toward various glycoproteins, such as immunoglobulins (Wilchek, M., and Bayer, E. A., *Meth. Enzymol.* 138:429–442 (1987)), for attaching these molecules to liposomes.

Gallium 67-labelled, hydrazide end-functionalized PEG liposomes were injected in rats by tail vein injection at about 10–20 micromolar phospholipid/kg body weight. Blood samples were obtained by retroobital bleeding at defined times. The percent of gallium labelled liposomes remaining in the bloodstream was determined at 0, 15 minutes, 1, 3, 5, and 24 hours and is presented in Table 3. The percent injected gallium 67-labelled liposome dose remaining in the blood stream at different times is illustrated in a half log plot versus time in FIG. 12.

After 24 hours the animals were sacrificed and tissues removed for label quantitation. The percent of the injected dose found in selected tissues at 24 hours is presented in Table 3.

The blood and tissue retention of Ga-labelled, hydrazide end-functionalized liposomes having two different lipid compositions were also compared as shown in Table 3. A fluid liposome composition was prepared from partially hydrogenated egg phosphatidylcholine (PHEPC). A typical liposome composition contains the hydrazide PEG-DSPE lipid, partially hydrogenated egg PC (PHEPC), and cholesterol in a lipid:lipid:lipid mole ratio of about 0.15:1.85:1. A rigid liposome composition was prepared by substituting hydrogenated serum phosphatidylcholine (HSPC) for PHEPC at the same mole ratio.

As is indicated in Table 3, the fluidity of the liposome composition does not affect the blood retention time of the liposomes. However, the fluidity of the liposome composition does appear to affect the tissue distribution of the end-functionalized liposome. For example, rigid liposomes are preferentially retained by liver, spleen and bone tissue. Fluid liposomes are preferentially retained by the kidneys, heart, skin and muscle tissue.

TABLE 3

% Injected 67 GA Dose Detected at Specified Timepoints

|  | Peg-HZ Rigid | PEG-Hz Fluid |
|---|---|---|
| Blood |  |  |
| 0 | 101.1 ± 12.0 | 100.2 ± 5.4 |
| 15 min. | 89.6 ± 11.2 | 81.6 ± 2.5 |
| 1 hr. | 84 ± 11.1 | 81.7 ± 7.4 |
| 3 hr. | 76 ± 10.5 | 75.3 ± 5.1 |
| 5 hr. | 71.7 ± 10.7 | 66.3 ± 3.8 |
| 24 hr. | 33.4 ± 6.8 | 34.3 ± 0.68 |
| Tissues at 24 hr. |  |  |
| liver | 12.1 ± 1.2 | 8.8 ± 0.81 |
| spleen | 5.1 ± 0.47 | 4.7 ± 0.64 |
| kidneys | 1.4 ± 0.22 | 1.7 ± 0.25 |
| heart | 0.36 ± 0.037 | 0.77 ± 0.21 |
| lungs | .62 ± 0.23 | 0.58 ± 0.03 |
| skin | .086 ± 0.03 | 0.16 ± 0.08 |
| muscle | .08 ± 0.03 | 0.29 ± 0.02 |
| bone | .28 ± 0.09 | 0.04 ± 0.01 |

IV. Therapeutic Effector Compositions

Below are described specific embodiments of the effector composition of the invention, and their intended use as injectable therapeutic agents.

A. Compositions for Enhancing an Immune Response

In one general embodiment, the effector in the liposome composition is a molecule capable of enhancing an immune response when administered parenterally.

1. $F_{ab}$ Effector. The $F_{ab}$ effector composition is used as a passive vaccine to provide humoral immunity against one of a variety of selected pathogenic antigens. The composition is administered to supplement a weakened immune response to a given antigen.

The vaccine effector composition is administered intravenously shortly after exposure to, or shortly before expected exposure to a selected pathogen. The composition is preferably injected in an amount corresponding to between about 0.1 to 2 mg antibody/kg body weight. After IV administration, the composition circulates in the blood-stream, at an effective concentration, for 1–2 days.

2. CD4 Glycoprotein Effector. Numerous therapies for the prevention and treatment of human immunodeficiency virus (HIV) infection and acquired immune deficiency syndrome (AIDS) have been proposed. These therapies target different steps in the process of viral infection. Frequently, therapy includes the administration of drugs which interfere with viral replication, such as AZT and DDI. The administration of these drugs is accompanied by toxic side effects, since the replication process of normal cells is also affected.

Another step in the process of viral infection which is targeted in therapy is viral attachment to cells. HIV binds with specificity to the CD4 receptor of CD4+ T cells. By mechanisms not yet fully understood, the CD4+ cells eventually can become infected by HIV. Soluble CD4 receptor polypeptides have been administered intravenously to HIV-infected patients to prevent further HIV infection of a patient's CD4+ T cell population. Heretofore, this therapy has not been effective, since CD4 receptor fragments are rapidly cleared from circulation in the blood stream, and inhibitory plasma concentrations cannot be maintained (Capon and Ward).

The effector molecule in this embodiment is a soluble CD4 receptor polypeptide capable of binding to the gp120 glycoprotein of human immunodeficiency virus (HIV) to prevent binding of HIV to CD4+ T cells. In a preferred embodiment covalent attachment of CD4 is accomplished by coupling periodate oxidized CD4 with hydrazide group containing liposomes.

CD4 administered as a long-circulating liposomal composition will remain in the blood stream for a longer period of time. The CD4 effector composition can be administered intravenously during early or late stages of HIV infection, most beneficially in combination with other drugs used in AIDS therapeutics, so that HIV particles bound to the liposomes, to the extent these are taken up by infected cells, will also deliver a dose of the anti-viral agent to the infected cells. AZT and DDI are examples of anti-HIV drugs which may be encapsulated in the liposome compositions.

The liposome composition should be administered intravenously in a dose equivalent to an effective blood stream CD4 concentration of 1–10 micromolar. Doses of 5–40 mg CD4/kg body weight can be administered, typically at intervals of 2–14 days between treatments, with the level of HIV present in the bloodstream being monitored during treatment by standard assay methods.

Principal advantages of this composition are the increased circulation time of the CD4 effector in the blood stream and the polyvalent presentation of the effector on the surface of the liposomes. Improved affinities of polyvalent CD4 presentation has recently been described (Chen, L. L., et al., *J. Biol. Chem.* 266:18237–18243 (1991)). As described above, CD4 receptor fragments are cleared rapidly by renal filtration. Covalent attachment of the CD4 polypeptide to liposomal carriers prevents renal clearance, and permits circulation of the polypeptide effector composition for 24–48 hours in the blood stream.

Additionally, the polyvalent CD4-bearing liposomes resemble CD4+ T cell lymphocytes in that the CD4 glycoproteins are presented on hydrophobic surfaces which mimic the surfaces of T cell lymphocytes. This presentation is likely to serve as a decoy binding HIV particles and HIV infected cells expressing gp120 so that healthy CD4+ lymphocytes are spared.

3. Effector for Stimulating Inflammatory Immune Responses. Some medical conditions are treated indirectly, by stimulation of the body's natural immune response. Such conditions can include immunodeficiency diseases, such as AIDS, chronic infectious, and certain types of cancers. One immunostimulant therapy involves intravenous injection of cytokines, which can acts to stimulate B cell and T cell immune responses in a variety of ways.

The cytokine effector composition may be administered on a short term basis to enhance a weak immunogenic or weak microbicidal response. Alternatively, the cytokine effector composition may also be administered on a long term basis as part of a therapy treatment for cancer or AIDS. The effector composition may be administered intravenously at doses of about 0.5 to 5.0 mg/kg body weight to enhance an immunogenic response. These doses result in an effective cytokine concentration of about 0.1–1 micromolar in the blood stream.

B. Compositions for Blocking Binding to Cell Receptors

In another general embodiment, the effector in the liposome composition is a molecule capable of blocking the binding of an endogenous agent to a cell receptor, to achieve a desired therapeutic effect.

1. ELAM-1 Binding Inhibitor. As one example, inflammation causes the expression of a polypeptide, endothelial leukocyte adhesion molecule-1 (ELAM-1), on the surface of endothelial cells of the blood vessels. ELAM-1, in turn, recognizes and binds a polysaccharide moiety on surfaces of neutrophils, and recruits neutrophils to sites of inflammation. By preventing the recognition and binding of neutrophils by ELAM-1, excessive inflammatory responses due to conditions, such as reperfusion injury, septic shock, and chronic inflammatory diseases, can be avoided.

In this embodiment, the effector is used to prevent the excessive recruitment of neutrophils to sites of inflammation in the blood stream. The effector is sialyl Lewis$^x$ recognized by ELAM-1 (Phillips). This polysaccharide effector is covalently attached to long-circulating liposomal compositions by the methods described above. In a preferred embodiment attachment of sialyl Lewis$^x$ to liposomes is accomplished via the reducing end of the glucosamine residue. The reducing end can easily react with a hydrazide group of a DSPE-PEG preparation. Coupling of the polysaccharide to the liposomal carrier composition prevents the polysaccharide's clearance by the kidney, and maintains an effective concentration of the polysaccharide effector over a 48 hour period. The liposomal carrier composition is administered in doses of 10 to 50 micrograms/kg body weight in a timely fashion, intravenously, and close to the site of inflammation.

2. Inhibitor of IL-1 Activity. As a second example, the effector is IL-1 inhibitor, which inhibits IL-1's immunostimulatory activity, or IL-1 receptor antagonist (IL1RA), which blocks the binding of IL-1 to lymphocyte cell surfaces. These molecules may be administered to a subject for treatment of septic shock, toxic shock, colonic inflammation, or leukemic cell proliferation. In this aspect of the invention, the liposomal carrier composition is administered in doses of 20 to 50 micrograms/kg body weight on a short term basis for the treatment sepsis, toxic shock or colonic inflammation. The liposomal carrier composition may also be administered at 1 to 2 day intervals on a long term basis for the treatment of leukemia.

Other molecules effective to block the binding of specific cytokines to specific lymphocyte populations may also be employed.

The use of the long-circulating effector composition, for use in blocking the binding of endogenous agents to cell receptor sites, provides two advantages over the use of free effector. First, the effector is maintained in the bloodstream over an extended period, by virtue of blocking renal clearance of the effector. Secondly, the effector molecule, in liposome-bound form, provides greater steric hindrance at the cell surface site of the receptor. Also, the competitive binding or blocking effector and endogenous agent on the receptor site is shifted toward the blocking agent, since the liposomal structure will be displaced at a slower rate kinetically, due to its larger size and number of blocking molecules in the region of the receptor site.

3. Peptide Hormones. In this embodiment the effector composition is useful in the treatment of various diseases that respond to peptide hormones. In one embodiment, the effector is parathyroid hormone (PTH) which is effective to inhibit uncontrolled osteoblast division.

4. Peptide. In this embodiment, the effector is a short peptide that has cell-binding activity and is effective to compete with a ligand for a receptor site. Inhibition of the ligand-receptor cell-binding event potentially results in arresting the infection process.

In general, useful peptides will have cell-binding activity due to a portion of sequence other than the end of the peptide. In this way, after attachment to the polymer chain on the liposome, the peptide remains active. Another general feature of useful peptides is their small size. Peptides of between about 4–20 amino acids are preferred.

One exemplary peptide, YIGSR, identified herein as SEQ ID NO:6 (FIG. 13), is useful for blocking metastases of tumors. SEQ ID NO:6 is one of the peptide sequences in the Bl chain of laminin responsible for the glycoprotein's adhesive properties and is known to bind to the laminin receptor. Laminin, the protein in which the YIGSR sequence occurs, is a constituent of basement membranes. Circulating metastatic cells which over-express the laminin receptor may find their way to laminin molecules in the basement membrane where they may become attached and establish metastatic tumors. By introducing exogenous YIGSR, the laminin receptors of circulating metastatic cells are blocked, thereby inhibiting tumor establishment.

Similarly, the peptide arginine-glycine-aspartic acid-serine (RGDS) has experimentally been shown to inhibit the establishment of metastatic tumors by interfering with the binding of tumor cells to fibronectin (Humphries, M. J., et al., *Science* 233:467–469 (1986)). Like YIGSR, RGDS is a peptide sequence involved with tumor cell adhesion to basement membranes.

The infection of lymphocytes by HIV also involves a specific peptide-receptor interaction (Nehete, P. N., et al., *J.*

Figures 12, 13:
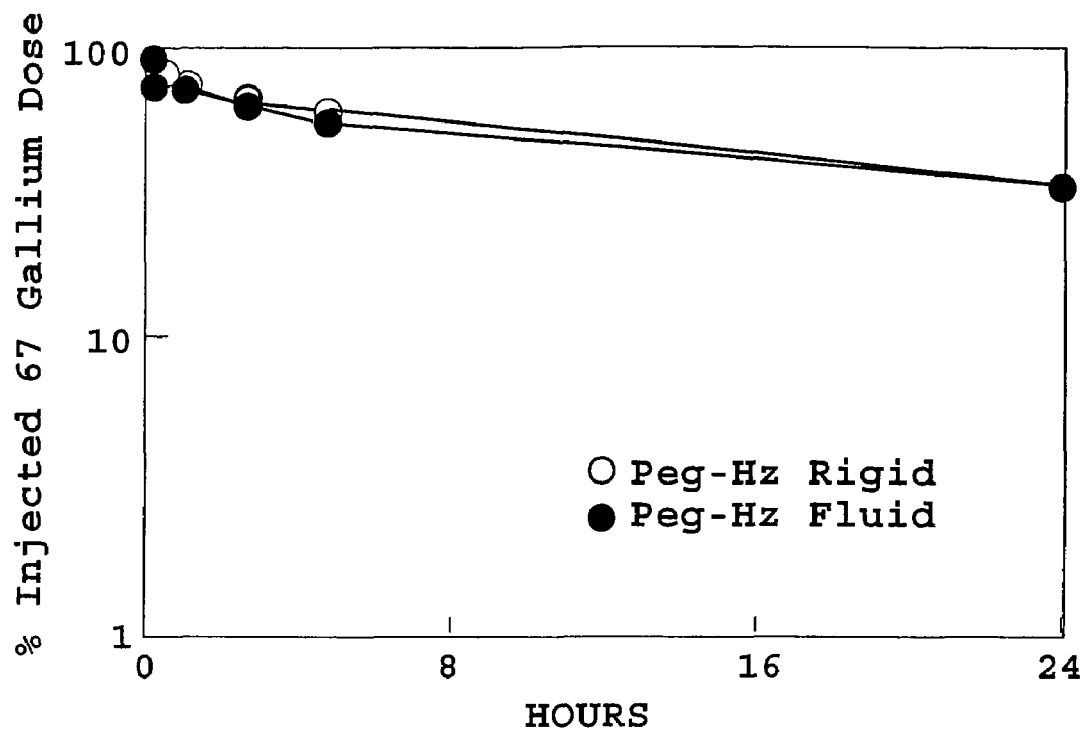
FIG. 12 shows a plot of a time course of gallium-67 labelled liposomes composed of hydrazide PEG-DSPE, partially hydrogenated egg phosphatidylcholine (PHEPC), and cholesterol (PEG-HZ fluid liposomes) or hydrazide PEG-DSPE, hydrogenated serum phosphatidylcholine (HSPC), and cholesterol (PEG-HZ rigid liposomes) in the bloodstream.
FIG. 13 shows the amino acid sequences for peptides identified by SEQ ID NOS:1–10, in conventional single-letter amino acid code.

Virol. 67:6841–6846 (1993)). Here, the receptor is the CD4 protein and the peptide is the HIV envelope protein gp120. The peptide binding sequences are located in the V3 loop of gp120. Several peptide sequences of between 8–15 amino acids have been implicated in the binding interactions. These sequences include SEQ ID NO:1 through SEQ ID NO:5 and are shown in FIG. 13.

*Pseudomonas cepacia* infections also exhibit specific binding to the cells they infect (Sajjan, U. S., et al., *Inf. Immun.* 61:3157–3163 (1993)). *Pseudomonas* pilin proteins, which are found on the bacterial cell surface, act as receptors for host proteins called mucins. Suitable peptides have been disclosed (e.g., Sastry, P. A., et al., *J. Bacteriology* 164(2): 571–577 (1985); Lee, K. K., et al., *Molecular Microbiol.* 3(11):1493 (1989)).

C. Antimicrobial Composition

In this embodiment the effector is a compound which is useful in the prevention and treatment of septic shock. The causal agents of septic shock are endotoxins which accumulate during systemic gram-negative bacterial infections (Jawetz, E., in *BASIC AND CLINICAL PHARMACOLOGY* (Katzung, B. G., Ed.) Apple & Lange, Los Altos, Calif., pg. 511 (1987)). Because of the rapid onset of severe sepsis, treatment is often not begun until critical stages of sepsis.

The antimicrobial agent which has been used most successfully in treating septic shock against in cases of septic shock is polymyxin B. Because the compound is rapidly excreted, high doses of polymyxin B are required for effective treatment. The high doses, unfortunately, can lead to severe renal toxicity.

In the present invention, polymyxin B circulation in the bloodstream is extended severalfold by its attachment to long-circulating liposomes. The compound is attached to long-circulating liposomal composition carriers by the coupling methods described above.

The liposomal composition is administered on a short term basis, at a dose of 0.1–0.5 mg/kg body weight, as a prophylactic for individuals at risk of, or suffering from acute septic shock. Features of the polymyxin B liposomal composition, already discussed, will minimize polymyxin B's renal accumulation and renal toxicity.

The following examples illustrate methods for preparing derivatized lipids and protein-coated liposomes in accordance with the invention.

EXAMPLE 1

Preparation of DSPE-PEG-Maleimide

A. Preparation of the Mono 2-nitrobenzene-sulfonamide of PEG bis(amine) (Compound II)

A mixture of 1.7 g (0.5 mmole) of commercially available polyethylene glycol bis(amine) and 104 mg (0.55 mmole) of 2-nitrobenzene sulfonyl chloride were added to a round-bottomed flask. The minimum amount of dioxane to effect solution (about 15 mL) and 280 microliters of triethylamine (2 mmole) were added. The reaction flask was stoppered and allowed to stand at room temperature for 4 days.

Thin layer chromatography (TLC) on silica coated plates using a solvent mixture of the following composition $CHCl_3$:$CH_3OH$:$H_2O$:$NH_4OH$, 130:70:8:0.5 (v/v/v/v), showed fluorescence quenching spots at $R_f$=0.87 to 0.95 and $R_f$=0.68–0.75. The 2-nitro benzene sulfonyl chloride was a more compact spot at $R_f$=0.85. The UV absorbing material at $R_f$=0.87–0.95 was tentatively identified as the bis-2-nitrobenzenesulfenamide. The material at $R_f$=0.68–0.75 was assigned to the desired mono-2-nitrobenzenesulfonamide of the starting diamine.

The solvent was evaporated under vacuum to obtain 2.135 g of a yellow syrup. The crude syrup was dissolved in 5 mL chloroform and placed at the top of a 21 mm×270 mm column of $SiO_2$ wetted with chloroform. The product was purified by passing through the column, in sequence:

| Amount (mL) | Volume % Chloroform | Volume % MeOH containing 1% conc. $NH_4OH$ |
|---|---|---|
| 100 | 100% | 0% |
| 200 | 90% | 10% |
| 100 | 80% | 20% |
| 100 | 70% | 30% |

Fifty mL aliquots were collected separately and assayed by TLC as described above. Most of the yellow, ninhydrin positive-reacting material was eluted in the 20% MeOH fraction. The fractions were dried and resulted in recovery of 397 mg of a bright yellow solid. The yield of the pure sample was about 20%.

B. Preparation of the Imidazole Carbamide of the Mono 2-nitrobenzenesulfonamide of PEG bis(amine)(Compound III)

550 mg (0.15 mmole) of the 2-nitrobenzenesulfonamide of PEG bis(amine), compound II, were dissolved in anhydrous benzene. To this was added 49 mg of carbonyl diimidazole (0.3 mmole) and 28 microliters (0.20 mmole) of triethylamine. The air in the reaction vessel was displaced with nitrogen, the flask sealed and the reaction mixture was heated in an 80° C. oil bath for 4 hours. TLC on silica-coated plates using the same solvent system as described above showed that all of the starting sulfonamide ($R_f$=0.72) had been consumed, and had been replaced by an iodine absorbing material at $R_f$=0.92. The solvent was removed under vacuum. The residue was dissolved in about 2.5 mL chloroform and transferred to the top of a 21×280 mm column of silica which was wetted with chloroform. The following solvents were passed through the column, in sequence:

| Amount (mL) | Volume % Chloroform | Volume % MeOH containing 1% conc. $NH_4OH$ |
|---|---|---|
| 100 | 100% | 0% |
| 100 | 90% | 10% |
| 200 | 80% | 20% |

50 mL fractions were collected and assayed by TLC. The desired product, compound III, was found predominantly in the 80-20 chloroform-methanol fractions. Upon evaporating the pooled fractions to dryness, 475 mg of a lemon-yellow solid was obtained (compound III).

C. Preparation of the DSPE carbamide of the 2-nitrobenzene sulfonamide of PEG bis(amine)

To the 450 mg (0.125 mmole) of 2-nitrobenzenesulfonamide of the imidazole carbamide of PEG bis(amine) (compound III) dissolved in 4.5 mL benzene was added 93 mg DSPE (0.125 mmole) and 70 microliters (0.50 mmole) of triethylamine. The reaction flask was then flushed with nitrogen, stoppered, and the contents heated in an oil bath at 80° C. for 6 hours with stirring. The reaction mixture was then cooled to room temperature and analyzed by TLC. TLC indicated that all of the DSPE had been consumed (e.g., the reaction had gone to completion). The solvent was evaporated under vacuum and the residue was dissolved in 2.5 mL chloroform and placed at the top of a 21×260 mm column of silica wetted with chloroform. The sample was purified by passing through the column in sequence:

| Amount (mL) | Volume % Chloroform | Volume % MeOH containing 1% conc. NH$_4$OH |
|---|---|---|
| 100 | 100% | 0% |
| 200 | 90% | 10% |
| 100 | 80% | 20% |
| 100 | 70% | 30% |

The desired product eluted at 20% (1% conc. NH$_4$OH in MeOH), was evaporated and afforded 358 mg of a bright yellow solid with an $R_f$=0.95. Fractions containing imidazole were not used and the final yield of the product (0.0837 mmoles) was 65%.

D. Preparation of the DSPE Carbamide of PEG bis (amine) (Compound IV)

The product from Example 1C above (~358 mg) was dissolved in 10 mL ethanol. To this solution was added 2.4 mL water and 1.2 mL acetic acid. The mixture was allowed to stand at room temperature for 18 hours. TLC analysis after 18 hours indicated that only partial deprotection had occurred. To the reaction mixture was added another 2.3 mL water and 1.2 mL acetic acid and the reaction mixture was then allowed to stir overnight. TLC analysis on silica-coated plates using a similar solvent system as described above revealed florescence quenching materials with $R_f$ values of 0.86 and 0.74, respectively. The desired ninhydrin reactive, phosphate-containing material migrated with an Rf value of 0.637. This spot showed no fluorescence quenching.

The solvent was removed under vacuum. The remaining residue was redissolved in 15 mL chloroform and extracted with 15 mL 5% sodium carbonate. The mixture was centrifuged to effect separation, and the sodium carbonate phase was reextracted 2× with 15 mL chloroform. The combined chloroform extracts were evaporated under reduced pressure to obtain 386 mg of wax. TLC indicated that the wax was largely a ninhydrin positive, phosphate containing lipid of $R_f$=0.72.

The wax was dissolved in 2.5 mL chloroform and placed on a silica column which had been wetted with chloroform. The following solvents were passed through the column in sequence:

| Amount (mL) | Volume % Chloroform | Volume % MeOH containing 1% conc. NH$_4$OH |
|---|---|---|
| 100 | 100% | 0% |
| 200 | 90% | 10% |
| 100 | 80% | 20% |
| 100 | 70% | 30% |
| 100 | 50% | 50% |
| 100 | 0% | 100% |

The samples were assayed by TLC. The desired product was found in fractions containing 70-30 and 50-50 chloroform-methanol as eluent. These samples were combined and evaporated to dryness under vacuum to afford 91 mg (22 micromoles) of a viscous syrup.

E. Preparation of the Maleic Acid Derivative of the DSPE Carbamide of PEG bis(amine) (Compound V)

To 18 micromoles of the viscous syrup prepared in Example 1D above and dissolved in 1.8 mL chloroform was added 3.5 mg (36 micromoles) maleic anhydride and 5 microliters (36 micromoles) triethylamine. The stoppered flask containing the reaction mixture was allowed to stand at room temperature for 24 hours and the solvent was subsequently evaporated under reduced pressure. TLC on silica plates indicated that all of the starting material had been replaced by a ninhydrin-negative, phosphate containing material of $R_f$=0.79–1.00 (Compound V).

F. Preparation of the Maleimide of the DSPE carbamide of PEG bis (amine) (Compound VI)

The syrup was dissolved in 2 mLs acetic anhydride saturated with anhydrous sodium acetate. The solution was heated in a 50° C. oil bath for two hours. After cooling to room temperature, 10 mL ethanol was added to the contents of the flask and the volatile components were then evaporated under vacuum. This step was repeated twice to remove excess acetic anhydride and acetic acid. The resulting residue was taken up 1 mL chloroform and passed through a silica gel column using the following solvents in sequence:

| Amount (mL) | Volume % Chloroform | Volume % MeOH containing 1% conc. NH$_4$OH |
|---|---|---|
| 100 | 100% | 0% |
| 200 | 90% | 10% |
| 100 | 80% | 20% |
| 100 | 70% | 30% |

50 mL samples were collected and the main product was found in the fractions eluted with 90-10 chloroform-methanol. The fractions were combined and evaporated to dryness under vacuum to afford 52 mg of a pale yellow viscous oil, which by TLC migrated with an Rf of 0.98 and was determined to contain phosphate. 12.3 micromoles of product (compound VI) were obtained, corresponding to a yield of about 34%.

EXAMPLE 2

Preparation DSPE-PEG 3-(2-pyridyldithio) propionamide

The DSPE carbamide of PEG bis (amine) (compound IV, 50 micromoles) is dissolved in 3 mL of anhydrous methanol containing 50 micromoles of triethylamine and 25 mg of N-succinimidyl 3-(2-pyridyldithio) propionate (SPDP, Pierce, Rockford, Ill.). The reaction is carried out at room temperature for 5 hours under an argon atmosphere. Methanol is removed under reduced pressure, and the products are redissolved in chloroform and applied to a 10 mL silica gel column, using silica gel which has been previously activated at 150° C. overnight. A similar solvent system as described in Example 1 is used to purify the product. Analysis on TLC plates indicates a product (compound VIII) with an $R_f$=0.98 which reacts negatively with ninhydrin, contains phosphate and has no free sulfhydryl groups. When the product is treated with excess dithiothreitol, 2-thiopyridinone is released.

EXAMPLE 3

Preparation of a PEG-Derivatized PE Containing a Terminal Aldehyde Group

A. Preparation of 1-trimethylsilyloxy-PEG (Compound X)

15.0 gm (10 mmoles) of PEG MW 1500, (Aldrich Chemical, St. Louis, Mo.) was dissolved in 80 mL benzene. 1.40 mL (11 mmoles) of chlorotrimethyl silane (Aldrich Chemical Co.) and 1.53 mL (1 mmoles) of triethylamine was added. The mixture was stirred at room temperature under an inert atmosphere for 5 hours.

The mixture was filtered by suction to separate crystals of triethylammonium chloride and the crystals were washed with 5 mL benzene. Filtrate and benzene wash liquids were combined. This solution was evaporated to dryness under vacuum to provide 15.83 grams of colorless oil which solidified on standing.

TLC of the product on Si—$Cl_8$ reversed-phase plates using a mixture of 4 volumes of ethanol with 1 volume of water as developer, and iodine vapor visualization, revealed that all the polyglycol 1500 ($R_f$=0.93) had been consumed and was replaced by a material of $R_f$=0.82. An infra-red spectrum revealed absorption peaks characteristic only of polyglycols.

Yield of 1-trimethylsilyloxy-PEG, M. W. 1500 (compound X) was nearly quantitative.

B. Preparation of trifluoromethane sulfonyl ester of trimethylsilyloxy-PEG (Compound XI)

15.74 grams (10 mmol) of the crystalline 1-trimethylsilyloxy PEG obtained as described above (compound X) was dissolved in 40 mL anhydrous benzene and cooled in a bath of crushed ice. 1.53 mL (11 mmol) triethylamine and 1.85 mL (11 mmol) of trifluoromethanesulfonic anhydride obtained from Aldrich Chemical Co. were added and the mixture was stirred overnight under an inert atmosphere until the reaction mixture changed to a brown color.

The solvent was then evaporated under reduced pressure and the residual syrupy paste was diluted to 100.0 mL with methylene chloride. Due to the reactivity of trifluoromethane sulfonic esters, no further purification of the trifluoromethane sulfonyl ester of 1-trimethylsilyloxy PEG carried out.

C. Preparation of 1-Trimethylsilyloxy PEG 1500 PE Intermediate (Compound XII)

10 mL of the methylene chloride stock solution of the trifluoromethane sulfonyl ester of 1-trimethylsilyloxy PEG (compound XI) was evaporated to dryness under vacuum to obtain about 1.2 grams of residue (approximately 0.7 mmoles). To this residue, 3.72 mL of a chloroform solution containing 372 mg (0.5 mmoles) egg PE was added. To the resulting solution, 139 microliters (1.0 mmole) of triethylamine was added and the solvent was evaporated under vacuum. To the residue was added 5 mL dry dimethyl formamide and 70 microliters (0.50 mmoles) triethylamine (VI). Air from the reaction vessel was displaced with nitrogen. The vessel was sealed and heated in a sand bath at 110° C. for 22 hours. The solvent was evaporated under vacuum to obtain 1.58 grams of brownish colored oil.

A 21×260 mm column filled with Kieselgel 60 silica gel, 70–230 mesh, was prepared and wetted with a solvent composed of 40 volumes of butanone, 25 volumes acetic acid and 5 volumes of water. The crude product was dissolved in 3 mL of the same solvent and chromatographed using the above-described solvent system. Sequential 30 mL portions of effluent were each assayed by TLC.

The TLC analysis was carried out on silica gel coated glass plates using a solvent combination of butanone/acetic acid/water; 40/25/5; v/v/v. Visualization was carried out using iodine vapor absorption. In this solvent system, N-1-trimethylsilyloxy PEG-1500-PE appeared at $R_f$=0.78, Unreacted PE appeared at $R_f$=0.68.

The desired N-1-trimethylsilyloxy PEG 1500 PE was a chief constituent of the 170–300 mL portions of column effluent. When combined and evaporated to dryness under vacuum, these portions afforded 111 mg of a pale yellow oil (1-trimethylsilyloxy-PEG-1500-PE intermediate).

D. Preparation of Polyethylene Glycol 1500: PE (Compound XII)

Once-chromatographed, the trimethylsilyloxy intermediate from Example 3C above was dissolved in 2 mL of tetrahydrofuran. To this, 6 mL acetic acid and 2 mL water was added. The resulting solution was allowed to stand for 3 days at 23° C. The solvent from the reaction mixture was evaporated under vacuum and the resulting residue was dried to constant weight to obtain 75 mg of pale yellow wax. TLC on Si—C18 reversed-phase plates eluted with a solvent mixture of 4:1 ethanol-water (v/v) indicated that some free PE and some polyglycol-like material formed during the hydrolysis.

The residue was dissolved in 0.5 mL tetrahydrofuran and diluted with 3 mL of a solution of 80:20 ethanol:water (v/v). The solution was applied to the top of a 10 mm×250 mm chromatographic column packed with octadecyl bonded phase silica gel and the crude product was eluted with an 80:20 ethanol:water (v/v) solvent system, collecting sequential 20 mL portions of effluent. The effluent was assayed by reversed phase TLC. Fractions containing product (Rf=0.08 to 0.15) were combined. When evaporated to dryness under vacuum these portions afforded 33 mg of a colorless wax (compound XII) corresponding to a yield of only 3%, based on the starting phosphatidyl ethanolamine.

NMR analysis indicated that the product incorporated both PE residues and PEG residues. The product was used to prepare PEG-PE liposomes.

E. Preparation of the Aldehyde of PEG-PE (Compound XIII)

The free hydroxyl group on PEG derivatized PE (compound XII) can be oxidized to the corresponding aldehyde in the following manner (Harris, J. M., *J. Polym. Sci., Polym. Chem. Ed.* 22:341–352 (1984)) prior to incorporation of the functionalized polymers into liposomes. About 2.7 g PEG1500-PE (1 mmole), prepared as in Example 3D, is added to 0.4 g acetic anhydride in 15 mL dimethylsulfoxide and the resulting mixture is stirred for 30 hours at room temperature. The reaction mixture is then neutralized by addition of dilute sodium hydroxide and the solvent is evaporated under reduced pressure to yield a sticky residue.

The progress of the reaction may optionally be monitored by withdrawing aliquots of the reaction mixture, performing a mini work-up as described below, and monitoring the appearance of an IR absorption corresponding to an aldehyde group.

The sticky residue is dissolved in 10 mL chloroform, washed with two successive 10 mL portions of water, and the organic phase is dried over a drying agent such as anhydrous magnesium sulfate. The product-containing chloroform phase is evaporated under vacuum to obtain a wax. The wax is then redissolved in 5 mL chloroform and purified by column chromatography on silica gel using the following series of solvents:

| Volume % Chloroform | Volume % Methanol Containing 2% Conc. Ammonium Hydroxide/Methanol |
|---|---|
| 100% | 0% |
| 95% | 5% |
| 90% | 10% |
| 85% | 15% |
| 80% | 20% |
| 70% | 30% |
| 60% | 40% |
| 50% | 50% |
| 0% | 100% |

Typically, 50 mL fractions of column effluent are collected and analyzed by TLC on Si—C18 reversed-phase plates using a 4:1 ethanol:water (v/v) solvent system followed by $I_2$-vapor visualization.

Only those fractions containing an iodine-absorbing lipid with an $R_f$ value of about 0.20 are combined and evaporated to dryness under vacuum, followed by drying under high vacuum to constant weight to yield 94 mg of a waxy crystalline solid product (compound XIII) with a molecular weight of 2226.

EXAMPLE 4

Synthesis of N-hydroxysuccinimide ester of α-hydroxy-ω-(carboxymethylamino-carbonyl) PEG (Compound XXIV) and Coupling to DSPE An α-hydroxy-ω-carboxy derivative of PEG (compound XIX) (2 g, ≈1 mmol) and N-hydroxysuccinimide (0.23 g, 2 mmol) were dissolved in methylene chloride-ethyl acetate (4 mL, 1:1). The resulting solution was cooled in an ice-water bath and treated with dicyclohexylcarbodiimide (DCC) (0.25 g, 1.2 mmol) predissolved in ethyl acetate (1 mL). Within a few minutes the solution became cloudy as dicyclohexylurea (DCU) appeared. After 2 hours the reaction mixture was filtered to remove DCU and evaporated to dryness. The functionalized polymer was crystallized from isopropanol and dried in vacuo over $P_2O_5$. Yield: 1.5 g (70%).

Titration of the product for active acyl content (Zaplipsky, S., et al., *POLYMERIC DRUGS* (Dunn, R. L. and Ottenbrete, R. M., Eds.) American Chemical Society, pp. 91 (1991)) gave $4.8 \cdot 10^{-5}$ mole/g (104% of the theoretical value).

The N-hydroxysuccinimide ester of α-hydroxy-ω-carboxy-PEG (0.52 g, 0.2 mmol) was added to a suspension of DSPE (0.14 g, 0.185 mmol) in chloroform (2 mL) followed by addition of triethylamine (0.1 mL, 0.86 mmol). The mixture was heated in a water bath at 55° C. for 5 minutes, during which time the solution became clear. TLC (chloroform-methanol-water 90:18:2) on silica gel coated plates showed complete conversion of DSPE into a new product, which gave no color when treated with ninhydrin. The solution was treated with an equivalent amount of acetic acid to neutralize the TEA and the neutralized solution was evaporated to dryness. The residue was dissolved in water and extensively dialyzed through a 300,000 MWCO cellulose acetate membrane at 4° C., filtered (pore size 0.2 μm) and lyophilized, yielding pure compound XXIV (360 mg, ≈70%).

This compound may then be further reacted with DSC to form a PEG-derivatized DSPE lipid containing an α-succinimidyl carbonate group.

EXAMPLE 5

Preparation of DSPE-PEG-Hydrazide (Compound XXXII)

A. Preparation of ω-Hydroxy Acid Derivative of PEG, α-(Hydroxyethyl)-ω-(carboxymethyl-aminocarbonyl)oxy-poly(oxyethylene)(Compounds XIX and XXIX)

Polyethylene glycol (Fluka, PEG-2000, 42 g, 42 mequiv OH) is dissolved in toluene (200 mL), azeotropically dried (Zalipsky, S., et al., *Int. J. Peptide Res.* 30:740 (1987)) and treated with ethyl isocyanotoacetate (2.3 mL, 21 mmol) and triethylamine (1.5 mL, 10 mmol). The reaction mixture is stirred overnight at 25° C. and the solution is then evaporated to dryness. The residue is dissolved in 0.2 M NaOH (100 mL) and any trace of toluene is removed by evaporation. The solution is maintained at pH 12 with periodical dropwise addition of 4 M NaOH.

When the solution pH is stabilized at pH 12, the solution is acidified to pH 3.0 and the product is extracted with methylene chloride (100 mL×2). TLC on silica gel (isopropyl alcohol/$H_2O$/conc. ammonia 10:2:1) gives a typical chromatogram of partially carboxylated PEG (Zalipsky, et al., 1990) consisting of unreacted PEG ($R_f$=0.67), monocarboxylated derivative ($R_f$=0.55) and dicarboxylated derivative of the polymer ($R_f$=0.47). This solution is dried over anhydrous $MgSO_4$, filtered and evaporated to dryness. The PEG mixture is dissolved in water (50 mL). One-third of this solution (30 mL≈14 g of derivatized PEG) is loaded onto DEAE-Sephadex A-25 (115 mL of gel in borate form). After the underivatized PEG is washed off the column with water (confirmed by negative poly(methacrylic acid), PMA, test) (Zalipsky, et al., 1990), a gradient of ammonium bicarbonate (2–20 mM at increments of 1–2 mM every 200 mL) is applied, and 50 mL fractions are collected. Early eluting fractions, e.g., fractions 1–25, typically contain only PEG monoacid as determined by PMA and TLC analyses. These fractions are then pooled, concentrated to ≈70 mL, acidified to pH 2 and extracted with methylene chloride (50 mL×2). The $CH_2Cl_2$ solution is dried over anhydrous $MgSO_4$, concentrated and poured into cold stirring ether. The precipitated product (compound XXIX) is dried in vacuo. Yield: 7 g. Titration of carboxyl groups gives $4.6 \cdot 10^{-4}$ mequiv/g (97% of theoretical value).

B. Preparation of Compound XXX

Compound XXIX (5 g, 2.38 mmol) and tert-butyl carbazate (0.91 g, 6.9 mmol) are dissolved in $CH_2Cl_2$-ethyl acetate (1:1, 7 mL). The solution is cooled on ice and treated with DCC (0.6 g, 2.9 mmol) predissolved in the same solvent mixture. After 30 minutes the ice bath is removed and the reaction is allowed to warm to room temperature and stirred for an additional 3 hours. The reaction mixture is filtered to remove dicyclohexylurea and the resulting filtrate is evaporated to produce a crude residue. The residue is recovered and purified by two precipitations from ethyl acetate-ether (1:1) and dried in vacuo over $P_2O_5$. Yield: 5.2 g, 98%. TLC of the product reveals one spot ($R_f$=0.68) with an $R_f$ value different from that of the starting material ($R_f$=0.55). $^1$H-NMR (CDCl$_3$): δ 1.46 (s, t-Bu, 9H); 3.64 (s, PEG, 178H) 3.93 (br. d, J=4.5, $CH_2$ of Gly, 2H); 4.24 (t, C$\underline{H}_2$—OCO-Gly, 2H) ppm. $^{13}$C-NMR (CDCl$_3$): δ 28.1 (t-Bu); 43.4 ($CH_2$ of Gly); 61.6 ($CH_2OH$); 64.3 ($\underline{C}H_2OCONH$); 69.3 ($CH_2CH_2OCONH$); 70.5 (PEG); 72.4 ($\underline{C}H_2CH_2OH$); 81.0 ($CMe_3$); 155.1 (C=O of Boc); 156.4 (C=O of Gly urethane; 168.7 (C=O of Gly hydrazide) ppm.

C. Preparation of Compound XXXI

The ω-hydroxy Boc-hydrazide derivative of PEG (compound XXX, 5 g, 2.26 mmol) is dissolved in pyridine (1.1 mL), $CH_2Cl_2$ (5 mL) and $CH_3CN$ (2 mL) and treated with disuccinimidyl carbonate, DSC (1.4 g, 5.5 mmol). The reaction mixture is stirred at 25° C. overnight. The mixture is then filtered to remove solids and slowly added to cold ethyl ether (100 mL). The precipitated product is dissolved in warm ethyl acetate (45 mL), chilled and mixed with equal volume of ethyl ether. The precipitate is collected by filtration and dried in vacuo over $P_2O_5$. Yield of compound XXXI: 4.8 g, 90%.

Succinimidyl carbonate group content $4.15 \cdot 10^{-4}$ mequiv/g (98% of theoretical value) is determined by titration (Zalipsky, et al., 1991). $^1$H-NMR (CDCl$_3$): δ 1.46 (s, t-Bu, 9H); 2.83 (s, succinimide); 3.64 (s, PEG, 178H); 3.79

(t, C$\underline{H}_2$CH$_2$OCO$_2$-Su); 3.93 (br. d, J=4.5, CH$_2$ of Gly, 2H); 4.24 (t, C$\underline{H}_2$—OCO-Gly, 2H); 4.46 (t, C$\underline{H}_2$OCO$_2$—Su) ppm.

D. Preparation of Compound XXXII

To prepare the DSPE-PEG-hydrazide, a slight excess of succinimidyl carbonate Boc-protected PEG-glycine hydrazide (compound XXXI) is reacted with DSPE suspended in chloroform in the presence of triethylamine. The lipid derivative is quickly (5–10 minutes) solubilized during progress of the reaction. Excess heterobifunctional PEG is removed by dialysis using a 300,000 MWCO cellulose ester dialysis membrane from Spectrum. The recovered lipid conjugate is subjected to conventional Boc-deprotection conditions (4M HCl in dioxane for 30 minutes) and then further purified by recrystallization. H-NMR (CDCl$_3$): δ 0.88 (t, CH$_3$, 6H); 1.59 (t, C$\underline{H}_2$CH$_2$CO, 4H); 2.84 (t, CH$_2$CO, 4H); 3.64 (s, PEG, 180H); 4.0 (t); 4.2 (m, CH$_2$OCO—NH$_2$); 4.4–4.3 (two doublets); 5.2 (g, CH of glyceride).

EXAMPLE 6

Preparation of Liposomes with Covalently Bound β-Galactosidase

The maleimide of the DSPE carbamide of polyoxyethylene bis (amine) (3500-DSPE) was prepared as in Example 1. β-Galactosidase was purchased from Pierce (Rockford, Ill.). Enzyme assays with o-nitrophenyl galactose were performed essentially by monitoring the development of the colored product with an extinction coefficient of 4467 at 413 nanometers in 0.1 N sodium hydroxide. The assay mixture consisted of 86 mM sodium phosphate pH 7.3, 1 mM magnesium chloride, 50 mM beta-mercaptoethanol and 2.3 mM o-nitrophenyl galactose and product formation was monitored for 10 to 15 minutes in the linear range of the assay.

Liposomes (MLV's) were prepared according to standard methods with one of the compositions indicated in Table 4. The liposomes were sized by extrusion through a polycarbonate membrane to 200 nm.

TABLE 4

| "Phenotype" | | Mol % | | | | | |
|---|---|---|---|---|---|---|---|
| PEG-DSPE | Cross-linker | αT | Ch | Pc | Cross-linker | PEG-DSPE | PG |
| − | − | 1 | 33 | 61 | − | − | 5 |
| + | − | 1 | 33 | 61 | − | 5 | − |
| − | + | 1 | 33 | 56 | 5 | − | 5 |
| + | + | 1 | 33 | 56 | 5 | 5 | − | where α-T=α-tocopherol (antioxidant), Ch=cholesterol, PC=partially hydrogenated egg PC (IV 40), crosslinker=the maleimide derivative of PEG-3500-DSPE, and PG=egg phosphatidyl glycerol. In addition, all liposome preparations were "spiked" with a $^3$H-DPPC tracer. The total lipid concentration in each preparation, after hydration in PBS (50 mM sodium phosphate pH 7.2, 50 mM sodium chloride, was 2 mM.

Crosslinking reactions were performed by adding enzyme solution to the liposomes (final protein concentration=0.5 mg/mL) and incubating the suspension overnight at ambient temperature with gentle shaking. Unreacted crosslinker was then quenched with 10 mM 2-mercaptoethanol (2-ME) for 30–60 minutes at 37° C. Liposomes were separated from unconjugated protein by flotation through a metrizamide gradient: the sample was brought to 30% (w/v) metrizamide and transferred to an SW60Ti tube, 20% metrizamide was layered above, then PBS was added on top to provide an aqueous interface. Gradients were centrifuged at 45,000 rpm for 60 minutes at 4° C., then each liposomal band, easily visible at the PBS interface, was collected and transferred to dialysis tubing. Dialysis proceeded overnight at 4° C. against two changes of PBS. Removal of the metrizamide was necessary because it inhibits β-galactosidase activity significantly even at 1% (w/v) concentration.

EXAMPLE 7

Liposome Blood Lifetime Measurements of Hydrazide End-functionalized PEG Liposomes A. Preparation of Hydrazide End-functionalized Liposomes Hydrazide PEG-DSPE composed of PEG, end-functionalized with a hydrazide group, and distearyl-PE was prepared as described. The hydrazide PEG-DSPE lipid was combined with partially hydrogenated egg PC (PHEPC) and cholesterol in a lipid:lipid:lipid mole ratio of about 0.15: 1.85:1 and the lipid mixture was hydrated. Generally, lipid hydration occurred in the presence of desferal mesylate, followed by sizing to 0.1 micron, and removal of non-entrapped desferal by gel filtration with subsequent loading of Ga-oxide into the liposomes. The unencapsulated Ga was removed during passage through a Sephadex G-50 gel exclusion column. Both compositions contained 10 micromoles/mL in 0.15 M NaCl, 5 mM desferal.

A second lipid mixture was prepared in a similar manner but with HSPC (hydrogenated serum phosphatidylcholine) instead of PHEPC.

B. Measuring Blood Circulation Time and Tissue Levels

In vivo studies of liposomes were performed in laboratory rats weighing 200–300 g each. These studies involved tail vein injection of liposome samples at about 10–20 micromolar phospholipid/kg body weight. Blood samples were obtained by retroobital bleeding at defined times. The animals were sacrificed after 24 hours and tissues removed for label quantitation. The weight and percent of the injected dose in each tissue was determined. The studies were carried out using $^{67}$Ga-desferal loaded liposomes and radioactivity was measured using a gamma counter. The percent of the injected dose remaining in the blood at several time points up to 24 hours, and in selected tissues at 24 hours was determined as follows.

1. Plasma Kinetics of Hydrazide-PEG Liposomes.

The above-described liposome composition (0.4 mL) was intravenously administered and at times 0, 0.25, 1, 3, or 5 and 24 hours after injection, blood samples were removed and assayed for the amount of Ga-desferal present in the blood, expressed as a percentage of the amount measured immediately after injection.

Hydrazide-PEG liposomes have a blood halflife of about 15 hours, and nearly 30% of the injected material was determined to be present in the blood after 24 hours.

2. 24 Hour Tissue Levels

Studies to determine the distribution of gallium-labelled liposomes in selected tissues 24 hours after intravenous injection were performed. The liposome composition (0.4 mL) was intravenously administered as described in 7B above. The percent dose remaining in tissues 24 hours after intravenous administration is shown in Table 3.

While the invention has been described with reference to specific methods and embodiments, it will be appreciated that various modifications and changes may be made without departing from the invention.

The invention claimed is:

1. A liposome composition, comprising
   liposomes, each having an outer layer of hydrophilic chains, and
   an effector molecule attached to the distal ends of at least a portion of said chains,
   wherein said liposomes provide a polyvalent presentation of said effector molecule.

2. The composition of claim 1, wherein the effector molecule is selected from the group consisting of $F_{ab}$ antibody fragments, cytokines, cellular growth factors, peptide hormones, monosaccharides, polysaccharides, IL-1 inhibitors, ELAM-1 binding inhibitors, and *limulus antilipopolysaccharide* factor (LALF).

3. The composition of claim 2 wherein the polysaccharide is sialyl Lewis$^x$.

4. The composition of claim 2 wherein the cytokine is selected from the group consisting of interferons, interleukins, TNF, transforming growth factor β, lymphotoxin, GM-CSF, and G-CSF.

5. The composition of claim 4 wherein the interferon is selected from the group consisting of IFN-alpha, IFN-beta, and IFN-gamma.

6. The composition of claim 4 wherein the interleukin is selected from the group consisting of IL-1α, IL-1β, IL-2, IL-3, IL-4, IL-5, IL-6, IL-7, and IL-8.

7. A liposome composition for use in treating a condition mediated by binding of one binding member to a second binding member, comprising
   liposomes, each having an outer layer of hydrophilic polymer chains, and
   an effector molecule attached to the distal ends of at least a portion of said chains,
   wherein said liposomes provide a polyvalent presentation of said effector molecule.

8. The composition of claim 7 wherein the effector molecule is selected from the group consisting of Fab antibody fragments, cytokines, cellular growth factors, peptide hormones, monosaccharides, polysaccharides, IL-1 inhibitors, ELAM-1 binding inhibitors, and *limulus antilipopolysaccharide* factor (LALF).

9. The composition of claim 8 wherein the polysaccharide is sialyl Lewis$^x$.

10. The composition of claim 8 wherein the cytokine is selected from the group consisting of interferons, interleukins, TNF, transforming growth factor β, lymphotoxin, GM-CSF, and G-CSF.

11. The composition of claim 10 wherein the interferon is selected from the group consisting of IFN-alpha, IFN-beta, and IFN-gamma.

12. The composition of claim 10 wherein the interleukin is selected from the group consisting of IL-1α, IL-1β, IL-2, IL-3, IL-4, IL-5, IL-6, IL-7, and IL-8.

13. A liposome composition for use in treating a condition mediated by binding of one binding member, which is present in the bloodstream, to a second binding member, comprising
   liposomes, each having an outer layer of hydrophilic polymer chains, and
   an effector molecule attached to the distal ends of at least a portion of said chains,
   wherein said liposomes provide a polyvalent presentation of said effector molecule.

14. The composition of claim 13 wherein the effector molecule is selected from the group consisting of Fab antibody fragments, cytokines, cellular growth factors, peptide hormones, monosaccharides, polysaccharides, IL-1 inhibitors, ELAM-1 binding inhibitors, and *limulus antilipopolysaccharide* factor (LALF).

15. The composition of claim 14 wherein the polysaccharide is sialyl Lewisx.

16. The composition of claim 14 wherein the cytokine is selected from the group consisting of interferons, interleukins, TNF, transforming growth factor β, lymphotoxin, GM-CSF, and G-CSF.

17. The composition of claim 16 wherein the interferon is selected from the group consisting of IFN-alpha, IFN-beta, and IFN-gamma.

18. The composition of claim 16 wherein the interleukin is selected from the group consisting of IL-1α, IL-1 β, IL-2, IL-3, IL-4, IL-5, IL-6, IL-7, and IL-8.

19. A liposome composition for use in treating a condition mediated by binding of one binding member, which is a pathogen or cell in the bloodstream, to a second binding member comprising
   liposomes, each having an outer layer of hydrophilic polymer chains, and
   an effector molecule attached to the distal ends of at least a portion of said chains,
   wherein said liposomes provide a polyvalent presentation of said effector molecule.

20. The composition of claim 19 wherein the effector molecule is selected from the group consisting of Fab antibody fragments, cytokines, cellular growth factors, peptide hormones, monosaccharides, polysaccharides, IL-1 inhibitors, ELAM-1 binding inhibitors, and *limulus antilipopolysaccharide* factor (LALF).

21. The composition of claim 20 wherein the polysaccharide is sialyl Lewis$^x$.

22. The composition of claim 20 wherein the cytokine is selected from the group consisting of interferons, interleukins, TNF, transforming growth factor β, lymphotoxin, GM-CSF, and G-CSF.

23. The composition of claim 22 wherein the interferon is selected from the group consisting of IFN-alpha, IFN-beta, and IFN-gamma.

24. The composition of claim 22 wherein the interleukin is selected from the group consisting of IL-1α, IL-1β, IL-2, IL-3, IL-4, IL-5, IL-6, IL-7, and IL-8.

25. A liposome composition for use in treating a condition mediated by binding of one binding member to a second binding member, which is a target cell, comprising
   liposomes, each having an outer layer of hydrophilic polymer chains, and
   an effector molecule attached to the distal ends of at least a portion of said chains,
   wherein said liposomes provide a polyvalent presentation of said effector molecule.

26. The composition of claim 25 wherein the effector molecule is selected from the group consisting of Fab antibody fragments, cytokines, cellular growth factors, peptide hormones, monosaccharides, polysaccharides, IL-1 inhibitors, ELAM-1 binding inhibitors, and *limulus antilipopolysaccharide* factor (LALF).

27. The composition of claim 26 wherein the polysaccharide is sialyl Lewis$^x$.

28. The composition of claim 26 wherein the cytokine is selected from the group consisting of interferons, interleukins, TNF, transforming growth factor β, lymphotoxin, GM-CSF, and G-CSF.

29. The composition of claim 28 wherein the interferon is selected from the group consisting of IFN-alpha, IFN-beta, and IFN-gamma.

30. The composition of claim 28 wherein the interleukin is selected from the group consisting of IL-1α, IL-1β, IL-2, IL-3, IL-4, IL-5, IL-6, IL-7, and IL-8.

31. A liposome composition for use in treating a condition mediated by binding of one binding member, which is a pathogen, to a second binding member, which is a target cell, comprising
   liposomes, each having an outer layer of hydrophilic polymer chains, and
   an effector molecule attached to the distal ends of at least a portion of said chains,
   wherein said liposomes provide a polyvalent presentation of said effector molecule.

32. The composition of claim 31 wherein the effector molecule is selected from the group consisting of Fab antibody fragments, cytokines, cellular growth factors, peptide hormones, monosaccharides, polysaccharides, IL-1 inhibitors, ELAM-1 binding inhibitors, and *limulus antilipopolysaccharide* factor (LALF).

33. The composition of claim 32 wherein the polysaccharide is sialyl Lewis$^x$.

34. The composition of claim 32 wherein the cytokine is selected from the group consisting of interferons, interleukins, TNF, transforming growth factor β, lymphotoxin, GM-CSF, and G-CSF.

35. The composition of claim 34 wherein the interferon is selected from the group consisting of IFN-alpha, IFN-beta, and IFN-gamma.

36. The composition of claim 34 wherein the interleukin is selected from the group consisting of IL-1α, IL-1β, IL-2, IL-3, IL-4, IL-5, IL-6, IL-7, and IL-8.

37. A liposome composition for use in treating a condition mediated by binding of one binding member, which is a cell in the bloodstream, to a second binding member, which is a target cell, comprising liposomes, each having an outer layer of hydrophilic polymer chains, and an effector molecule attached to the distal ends of at least a portion of said chains, wherein said liposomes provide a polyvalent presentation of said effector molecule.

38. The composition of claim 37 wherein the effector molecule is selected from the group consisting of Fab antibody fragments, cytokines, cellular growth factors, peptide hormones, monosaccharides, polysaccharides, IL-1 inhibitors, ELAM-1 binding inhibitors, and *limulus antilipopolysaccharide* factor (LALF).

39. The composition of claim 38 wherein the polysaccharide is sialyl Lewis$^x$.

40. The composition of claim 38 wherein the cytokine is selected from the group consisting of interferons, interleukins, TNF, transforming growth factor β, lymphotoxin, GM-CSF, and G-CSF.

41. The composition of claim 40 wherein the interferon is selected from the group consisting of IFN-alpha, IFN-beta, and IFN-gamma.

42. The composition of claim 40 wherein the interleukin is selected from the group consisting of IL-1α, IL-1β, IL-2, IL-3, IL-4, IL-5, IL-6, IL-7, and IL-8.

43. A liposome composition for use in treating a condition mediated by binding of one binding member, which is a pathogen or a cell in the bloodstream, to a second binding member, which is a target cell, comprising liposomes, each having an outer layer of hydrophilic polymer chains, and an effector molecule attached to the distal ends of at least a portion of said chains, wherein said liposomes provide a polyvalent presentation of said effector molecule.

44. The composition of claim 43 wherein the effector molecule is selected from the group consisting of $F_{ab}$ antibody fragments, cytokines, cellular growth factors, peptide hormones, monosaccharides, polysaccharides, IL-1 inhibitors, ELAM-1 binding inhibitors, and *limulus antilipopolysaccharide* factor (LALF).

45. The composition of claim 43 wherein the polysaccharide is sialyl Lewis$^x$.

46. The composition of claim 43 wherein the cytokine is selected from the group consisting of interferons, interleukins, TNF, transforming growth factor β, lymphotoxin, GM-CSF, and G-CSF.

47. The composition of claim 46 wherein the interferon is selected from the group consisting of IFN-alpha, IFN-beta, and IFN-gamma.

48. The composition of claim 46 wherein the interleukin is selected from the group consisting of IL-1α, IL-1β, IL-2, IL-3, IL-4, IL-5, IL-6, IL-7, and IL-8.

* * * * *